United States Patent
Brass et al.

(10) Patent No.: US 6,177,678 B1
(45) Date of Patent: *Jan. 23, 2001

(54) METHOD AND APPARATUS FOR LEAK DETECTION AND NON-DESTRUCTIVE TESTING

(75) Inventors: Jack Brass, North York (CA); Thomas M. Lemons, Marblehead, MA (US)

(73) Assignee: Brasscorp Ltd. (CA)

( * ) Notice: Under 35 U.S.C. 154(b), the term of this patent shall be extended for 0 days.

This patent is subject to a terminal disclaimer.

(21) Appl. No.: 09/058,560

(22) Filed: Apr. 13, 1998

Related U.S. Application Data

(63) Continuation-in-part of application No. 08/755,851, filed on Dec. 9, 1996, now Pat. No. 5,804,822, which is a continuation of application No. 08/417,234, filed on Apr. 5, 1995, now abandoned.
(60) Provisional application No. 60/043,538, filed on Apr. 14, 1997.

(51) Int. Cl.$^7$ .................................................... G01N 21/64
(52) U.S. Cl. ...................... 250/461.1; 250/372; 250/365; 250/504 R; 250/504 H
(58) Field of Search ............................. 250/461.1, 459.1, 250/372, 365, 504 R, 504 H, 302

(56) References Cited

U.S. PATENT DOCUMENTS

| | | | |
|---|---|---|---|
| 2,525,914 | 10/1950 | Knauth | 73/229 |
| 3,136,890 | 6/1964 | Wain | 250/77 |

(List continued on next page.)

FOREIGN PATENT DOCUMENTS

| | | | |
|---|---|---|---|
| 2200364 | 5/1997 | (CA) | G01M/3/20 |
| 2200365 | 5/1997 | (CA) | G01N/21/19 |
| WO 98/20365 | 5/1998 | (WO) . | |

OTHER PUBLICATIONS

"Optimization Of Magnetic Powder Testing With Ultraviolet Light", Obering.N. Riess, Hamburg, 2034 Schweissen and Schneiden, 45 (1993), Juni, No. 6, Dusseldorf, DE.
"Short Arc Lamps: A Users Guide", from The Photonics Design & Appln. Handbook, 1990.
"Standard Practice For Liquid Penetrant Examination", ASTM, May 5, 1995.
"Standard Practice For Magnetic Particle Examination", ASTM, Nov.15, 1994.

\* cited by examiner

Primary Examiner—Seungsook Ham
Assistant Examiner—John Patti
(74) Attorney, Agent, or Firm—Fitzpatrick, Cella, Harper & Scinto

(57) ABSTRACT

A lamp system is for use in non-destructive testing to illuminate luminescent materials, such as fluorescent dyes. The lamp system has a control unit and a lamp. The lamp has a bulb and a filter. The bulb generates at least a first wavelength of invisible energy and the filter limits other visible wavelength light from the lamp. The lamp has a handle with a trigger. The control unit pulses the lamp on and off when the trigger is depressed. The lumiescent material absorbs the first wavelength of energy and pulses in response when the lamp illuminates the material. The system can be AC or DC operated. It can be operated from an automotive battery. A fault locating system for use with fluorescent dyes to detect faults in a body has a handheld D-type battery flashlight configuration with a casing having a handle at one end and a flared lamp housing at the other. A reflector fits within the lamp housing, and a bulb rests in the reflector. The bulb is an ultraviolet light source, for example tungsten halogen or a Xenon flashtube. A lens fits over an open end of the lamp housing to allow transmission of substantially more ultraviolet than visible light. The lens may be a dichroic filter. The bulb may be flashed to cause the fluorescent dye to re-emit pulses of light visible to the naked eye.

35 Claims, 23 Drawing Sheets

U.S. PATENT DOCUMENTS

| | | | |
|---|---|---|---|
| 3,590,256 | 6/1971 | Neeff | 250/218 |
| 3,666,945 | 5/1972 | Frungel | 250/71 |
| 3,736,428 | 5/1973 | Monroe | 250/71 |
| 3,875,094 | 4/1975 | Schroeter | 260/28 |
| 3,925,666 | 12/1975 | Allan | 250/338 |
| 3,953,763 | 4/1976 | Herrick | 315/262 |
| 4,048,490 * | 9/1977 | Troue | 240/41.35 |
| 4,112,335 | 9/1978 | Gonser | 315/241 |
| 4,229,658 | 10/1980 | Gonser | 250/504 |
| 4,270,049 | 5/1981 | Tanaka | 250/227 |
| 4,298,806 | 11/1981 | Herold | 250/504 |
| 4,336,459 | 6/1982 | Fay | 250/459 |
| 4,365,153 | 12/1982 | Seigel | 250/253 |
| 4,487,075 | 12/1984 | Karidis | 73/861 |
| 4,689,484 | 8/1987 | McMahon | 250/224 |
| 5,191,261 | 3/1993 | Mass | 315/171 |
| 5,200,801 | 4/1993 | Juvinall | 356/428 |
| 5,265,640 | 11/1993 | St. Amant | 137/114 |
| 5,804,822 * | 9/1998 | Brass et al. | 250/302 |

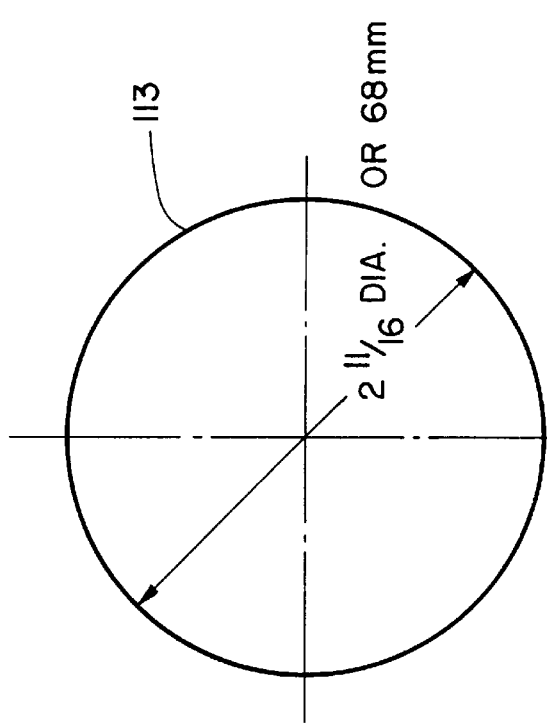
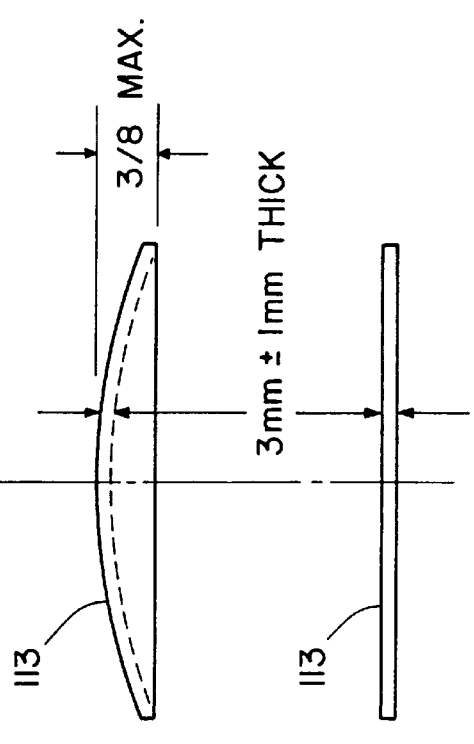
FIG. 11c  FIG. 11b  FIG. 11a

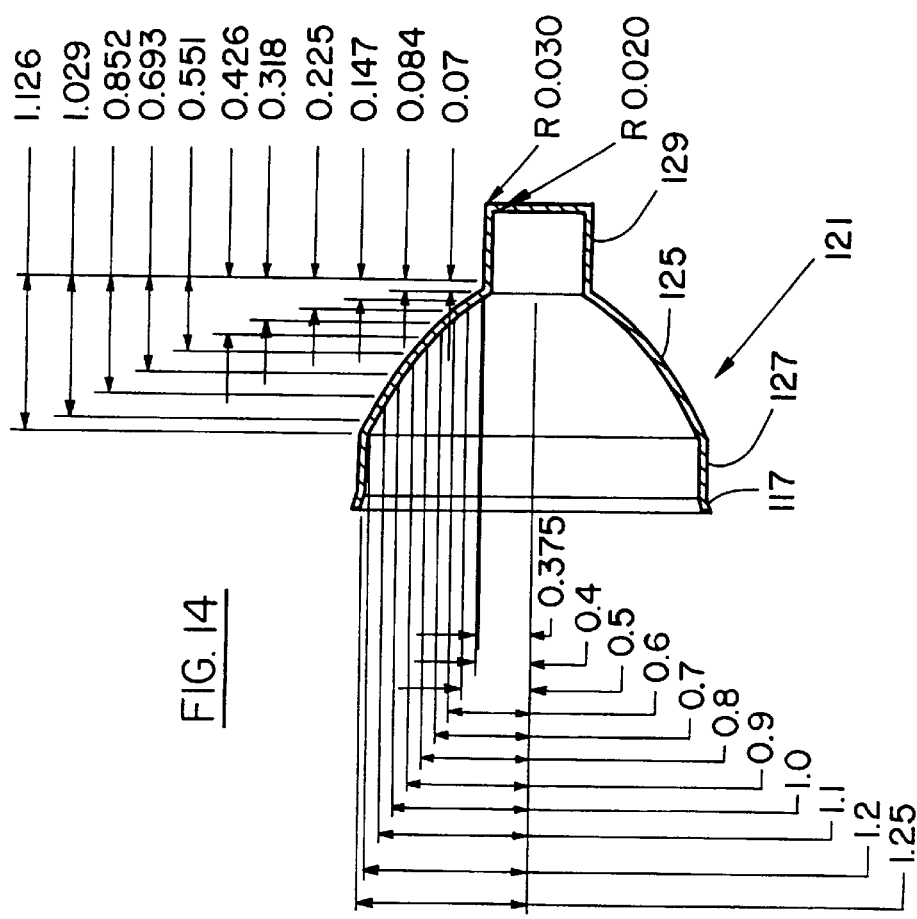
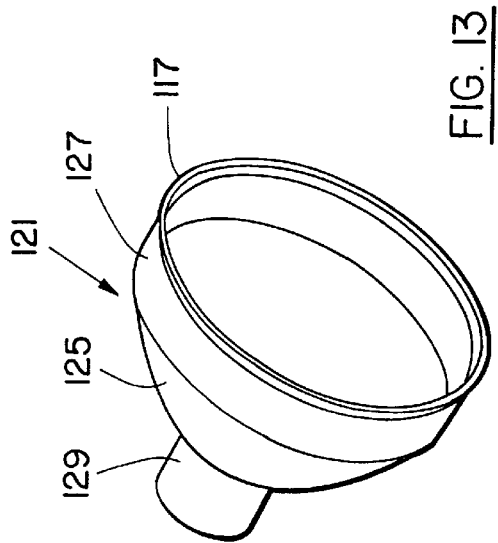
FIG. 14
FIG. 13

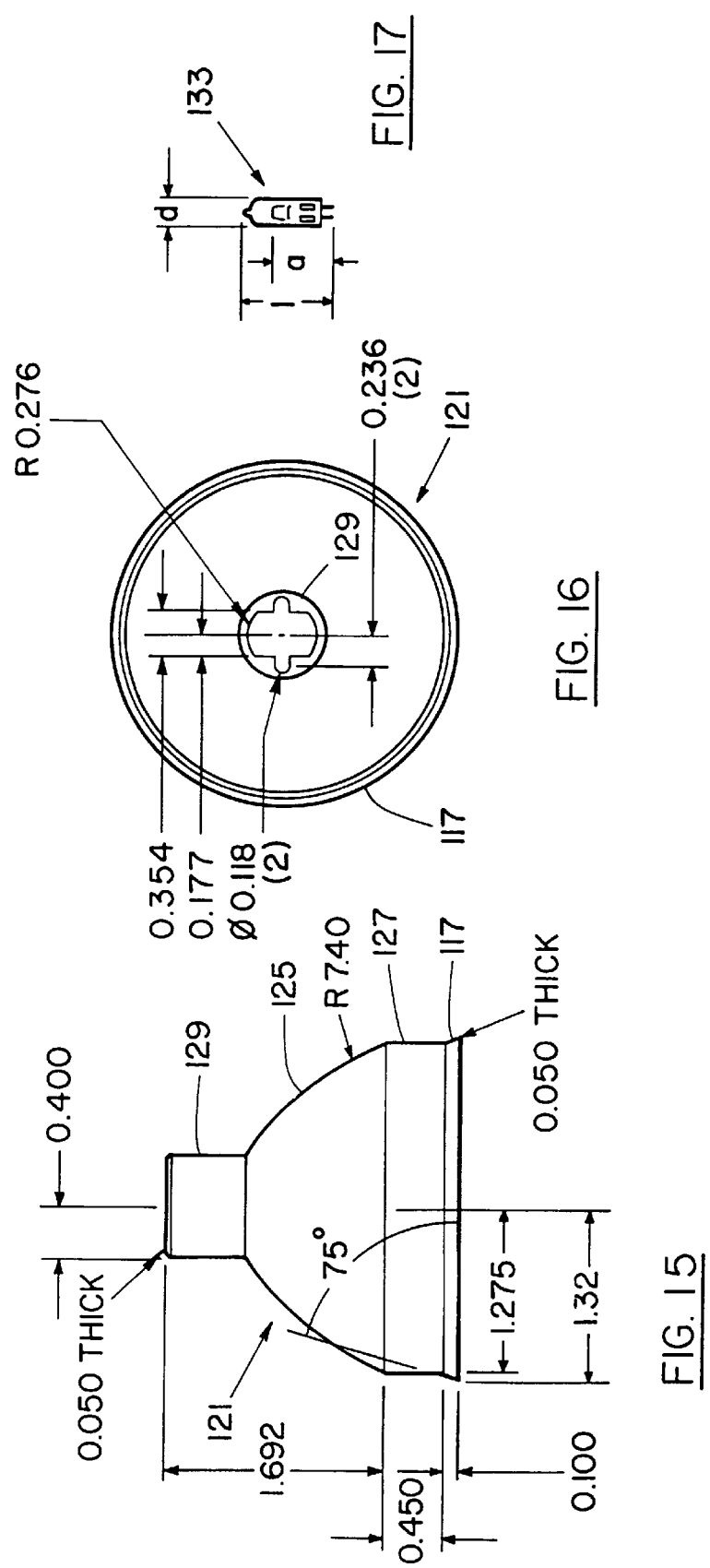

| | |
|---|---|
| Max Power input Pmax/W | |
| Nom Power Input Pnom/W | 3 |
| Max anode voltage Uamax/V | 400 |
| Nom anode voltage Uanom/V | 250 |
| Min Anode voltage Uamin/V | 150 |
| Nom Flashcapacitor CB/μF<br>tan at Hz | 2 |
| Series Inductance L/ μF | |
| Max peakcurrent Ip/A<br>at Ua = V | |
| Trigger coil TR HEIMANN | IS 1052 |
| Trigger capacitor Cz/ μF | 0.047 |
| Min trigger voltage Uzmin/V | 150 |
| Trigger contact S | TRIAC |
| Operation time/h | .60 |
| Life/number of flashes/N | |
| Light output bef life/ | |
| Light reduction aft life/ % | < 30 |
| Sec trigger voltage Uzsec/kV | -5.4 |
| Flash frequency f/Hz | 5-50 |

FIG. 22

| Reference | Quantity | Description | Value | Rating | Tolerance | Type | Footprint | Manufacturer | Manuf. P/N | Source |
|---|---|---|---|---|---|---|---|---|---|---|
| R1 | 1 | resistor | 47R | 2W | 5% | carbon | axial | | | Sayal |
| R2 | 1 | resistor | 2.7k | 1W | 5% | carbon | axial | | | Sayal |
| R3, R6 | 2 | resistor | 68k | 1/8W | 5% | carbon | axial | | | |
| R4 | 1 | resistor | 680k | 1/8W | 5% | carbon | axial | | | |
| R5 | 1 | resistor | 470R | 1/8W | 5% | carbon | axial | | | |
| R7 | 1 | resistor | 1k | 1/8W | 5% | carbon | axial | | | |
| R8 | 1 | resistor | 4.7k | 1/8W | 5% | carbon | axial | | | |
| R9 | 1 | resistor | 1M3 | 1/8W | 5% | carbon | axial | | | |
| C1, C2 | 2 | Capacitor | 0.1 uF | 100V | | ceramic | radial | | | |
| C3, C9 | 2 | Capacitor | 1uF | 50V min | | electrolytic | radial | | | |
| C4 | 1 | Capacitor | 0.01 uF | 100V | | ceramic | radial | | | |
| C5 | 1 | Capacitor | 10 uF | 50V | | electrolytic | radial | | | |
| C6 | 1 | Capacitor | 100 pF | 50V | | cermaic | radial | | | |
| C7, C8 | 2 | Capacitor | 33 uF | 450V | | electrolytic | radial | Panasonic "EB" | EEU-EB2W330S | Digi-Key |
| C10 | 1 | Capacitor | 0.047 uF | 1000V min | | ceramic | | | | Sayal |
| IC1 | 1 | IC | LM555 | | | timer | DIP-8 | | | |
| IC2 | 1 | IC | MCT2E | | | opto-coupler | DIP-8 | Motorla | | ABRA |
| IC3 | 1 | IC | 7812 | | | Voltage Reg | TO-220 | any | | |
| Q1, Q2 | 2 | NPN-SI | MJE182 | 60V/3A | | translator | | Motorla | | FAI |
| D1 | 1 | diode | 1N5400TR | 50V/3A | | Power | axial | FAI | | |
| D3, D4, D5, D6 | 4 | diode | 1N4007 | 1000V/1A | | Power | axial | | | |
| D2 | 1 | diode | 1N4148 | | | small sign | axial | | | |
| SCR | 1 | SCR | TIC106D | 400V/5A | | Thyristor | | | | |
| X1 | 1 | Flashtube | AGA0210 | 3W | | | | HEIMANN | | EG&G |
| T1 | 1 | xformer | PE-6194 | | | push-pull inverter | | PULSE ENG | | PULSE |
| T2 | 1 | xformer | ZS1052 | 1:36 | | pulse | | HEIMANN | | EG&G |
| L1 | 1 | inductor | 2uH | | | air-core | | | | Sayal |
| P1, P2, P3, P4, P5 | 5 | lug | 713330-8 | | | male | | | | |
| H1, H2 | 2 | heatsinks | | | | | | | | |

FIG. 26

METHOD AND APPARATUS FOR LEAK DETECTION AND NON-DESTRUCTIVE TESTING

This is a continuation in part of U.S. patent application Ser. No. 08/755,851 filed Dec. 9, 1996 (U.S. Pat. No. 5,804,822) by inventors Jack Brass and Steven Goldfarb entitled Fault Locating Device, System and Method, which is a continuation of 08/417,234 filed Apr. 5, 1995 (now abandoned). This application also has priority from United States provisional patent application of Jack Brass and Thomas M. Lemons filed Apr. 14, 1997 entitled Method and Apparatus for Leak Detection and Non-Destructive Testing, serial number unknown.

BACKGROUND OF THE INVENTION

Luminescent materials are often used to detect faults, such as leaks. For example, a fluorescent dye is injected or poured into a system. Where a leak occurs the dye will escape from the system. Shining a light of appropriate wavelength (typically ultraviolet) on the system will cause the dye to fluoresce. The existence and location of a leak or leaks are then evident. When performed in total darkness the outcome of such a procedure is often enhanced; however, total darkness is often not available in testing environments, such as an outdoor air conditioner where the sun cannot be shut off, or a shop floor where darkness may be dangerous when machinery in motion is involved.

Unfortunately, visible (including ambient) light competes with the fluorescence from dye for the attention of the person conducting the test. This is particularly true where the system has shiny surfaces that reflect visible or ambient light.

Similarly, luminescent materials are also used in non-destuctive testing. For example, fluorescent dyes combined with iron filings can be used to detect faults such as stress fractures. The combination of iron filings and fluorescent dye is attracted to the faults and, again, the dye emits visible light when illuminated by appropriate incident wavelength light. Even though non-destructive testing may be stringently regulated, the emitted light from a very small fault is often difficult to detect even though a very small fault may present a potentially great danger. Any assistance in identifying these faults would be helpful.

Other concerns with existing ultraviolet lamps are their cost, size and power consumption. For low power consumption and cost, fluorescent lamps can be used to generate the incident radiation. However, fluorescent lamps generate a low intensity of incident ultraviolet radiation. It is desirable to be able to bring the lamp in to close proimity with the fault. This is often difficult in the tight spaces available when working around machinery and equipment.

It is an object of the invention to address these or other problems associated with the use of lamps in the location of faults in machinery and equipment.

As described above in lamps for use in leak-detection and NDT are known. The basic method behind NDT and leak detection is simple. A fluorescent material is applied to a body to be tested in such a way as to highlight a fault in the body when the material is illuminated by shining a lamp emitting ultraviolet light of a particular wavelength on the body.

The fluorescent material can be applied to the body in many ways. The two most common are magnetic particles and liquid penetrants. Magnetic particles are mixed with fluorescent materials and applied to the body. The particles and fluorescent materials form distinctive patterns depending upon the characteristics of the body; for example, metal in aircraft components will act differently in the presence of magnetic fields and thus cause distinctive patterns of magnetic particles applied to the components, depending upon the existence of faults within the components. Such faults are typically caused by previous stresses. Liquid penetrants are also mixed with fluorescent materials to reveal faults by penetrating cracks in a body.

Stringent requirements for NDT lamps are specified in different standards, for example NDT using magnetic particles is covered in American Society for Testing and Materials ("ASTM") Standard Practice for Magnetic Particle Examination designation E 1444 and NDT using liquid penetrant is covered in ASTM Standard Practice for Liquid Penetrant Examination designation E 1417. Leak detection lamps are not typically covered in standards; but, typically benefit from properties required for NDT.

Designation E 1444 specifies the following for magnetic particle testing:

5.7 Lighting:

5.7.1 Visible Light—Visible light shall be used when examining with non-fluorescent particles. The intensity of the visible light at the surface of the part undergoing examination shall be maintained at a minimum of 100 fc (1000 1x). The intensity measurement shall be conducted with a suitable illuminance meter with a photopic spectral response.

5.7.1.1 Ambient Visible Light—Unless otherwise specified, fluorescent magnetic particle examinations shall be performed in a darkened area with a maximum ambient visible light level of 2 fc (20 1x) measured at the part surface.

5.7.1.2 Special Visible Internal Light Source—When examinations of internal surfaces must be performed using special visible light sources, the image produced must have sufficient resolution to effectively evaluate the required discontinuities. Light intensity shall be measured at the expected working distance of the equipment.

5.7.2 Black Lights—All black lights shall be checked at the intervals specified in Table 1, and after bulb replacement, for output. A longer period may be used if a plan justifying this extension is prepared by the nondestructive testing facility and approved by the contracting agency. The minimum acceptable intensity is 1000 $uW/cm^2$ at the part being examined. Black light reflectors and filters shall be checked daily for cleanliness and integrity. Damaged or dirty reflectors or filters shall be replaced or otherwise corrected as appropriate.

5.7.3 Internal Part Examination—Where lamps are physically too large to directly illuminate the examination surface, special lighting shall be used. Internal features such as bores, holes, and passages less than 0.5 in. (12.5 mm) nominal diameter shall not require magnetic particle examination unless otherwise specified by the contracting agency.

Designation E 1417 specifies similar lighting requirements.

In order to meet the low ambient light requirement and the high black light (ultraviolet A) requirement, a mercury vapour bulb is used with a coloured filter. The combination emits limited visible light and sufficient ultraviolet light.

While they produce relatively high amounts of ultraviolet light, mercury vapour bulbs are quite large and slow to turn on. Halogen bulbs have been used for leak detection with mixed results. Halogen bulbs turns on instantly; however, the bulbs produce limited amounts of ultraviolet light. Halogen bulbs are rarely used for NDT, if at all.

SUMMARY

In one aspect, the present invention provides a method for detecting faults in a body. The method includes the following steps: applying a fluorescent material to the body in a manner to concentrate the fluorescent material in a pattern indicative of the location of a fault in the body; activating a light source to emit ultraviolet output; filtering light from the light source through a filter which reflects substantially more visible light than the lens absorbs and which transmits substantially more ultraviolet light than it absorbs or reflects; shining the ultraviolet light transmitted from the filter on to the body.

The method may employ a filter that is an isotropic dichroic filter.

The method may also include a step of flashing the ultraviolet light at some time prior to shining the ultraviolet light on the body. The flashing is at a rate that causes the fluorescent material to produce corresponding fluorescent flashes which flashes are detectable to the human eye.

In a further aspect, the present invention provides a system for use with a body to be tested for faults using fluorescent material. The system includes a casing, a reflector, a bulb and a lens. The casing has an open end in which the reflector rests. The bulb sits within the reflector in such a manner to direct light emitted from the bulb through the open end of the casing. The lens encloses the open end of the casing in order to reflect substantially more visible light into the casing than the lens absorbs and to transmit from the system substantially more ultraviolet light than the lens absorbs or reflects.

The system may include a lens which is an isotropic dichroic filter.

The system may further include a control unit to flash the bulb at a rate that causes the fluorescent material to produce corresponding fluorescent flashes which flashes are detectable to the human eye. The bulb may be a flashtube. The flashtube may be a high pressure arc lamp Xenon flashtube.

In a further aspect, a system is for use with a body to be tested for faults using fluorescent material. The system has a handheld casing, a reflector, a high pressure arc lamp flashtube and a lens. The casing has an open end in which the reflector rests. The flashtube sits within the reflector in such a manner to direct light emitted from the flashtube through the open end of the casing. The lens encloses the open end of the casing in order to transmit from the system substantially more ultraviolet light than visible light.

The lens may be a dichroic filter that reflects into the system substantially more visible light than the filter absorbs and that transmits from the system substantially more ultraviolet light than the filter absorbs or reflects.

The passband of the filter may include the UVA range. The passband of the filter may be selected to substantially limit the transmission of visible and ultraviolet wavelengths outside the UVA range.

The system may include a control unit to flash the flashtube at a rate that causes the fluorescent material to produce corresponding fluorescent flashes which flashes are detectable to the human eye. The control unit may be contained within the casing. The control unit may flash the lamp at a fixed rate.

The system may draw approximately 300 mA of current from a 12 volt power source. The system may be operated from battery power contain within the casing. The battery power may be rechargeable.

The casing may have a D-type battery profile.

The reflector may focus the emitted light in a spot beam at a selected distance from the system. The selected distance may be approximately 18 inches. The beam may be approximately 200 mm in diameter at the selected distance.

The flashtube may be mounted axially within the reflector and centered on the reflector focal point. The reflector may be formed from non-high temperature plastic finished with an ultraviolet reflecting finish and a non-ultraviolet absorbing protective coating. The reflector may be finished with aluminum and coated with a non-ultraviolet absorbing coating. The coating may be silicon oxide. The coating may be silicon dioxide. The plastic may be a non-thermoset plastic.

The flashtube may be a hard glass flashtube. The flashtube may be an approximately 10 watt or less flashtube. The flashtube may be an approximately 5 watt or less flashtube. The flashtube may be a 3 watt flashtube.

The casing may be formed from non-high temperature plastic. The system may not be hot to the touch during operation.

BRIEF DESCRIPTION OF THE DRAWINGS

For a better understanding of the present invention and to show more clearly how it may be carried into effect, reference will now be made, by way of example, to the accompanying drawing which shows the preferred embodiments of the present invention and in which:

FIG. 11a is a side view of a lens used in the lamp system of FIG. 6, FIG. 11b is a cross-section of an alternative lens that could be employed in the system of FIG. 6, FIG. 11c is a plan view of the lens of FIG. 11a, FIG. 12a is a transmissiveness curve for the lens of FIG. 11a, FIG. 12b is an alternate transmissiveness curve for the lens of FIG. 11a, FIG. 13 is a perspective view of a reflector employed in the system of FIG. 6, FIG. 14 is a cross-section of the reflector of FIG. 13, FIG. 15 is a side view of the reflector of FIG. 13, FIG. 16 is an end view of the reflector of FIG. 13, FIG. 17 is a side view of a bulb employed in the system of FIG. 6, FIG. 26 is a parts list for the circuit diagram of FIG. 25.

DETAILED DESCRIPTION OF THE PREFERRED EMBODIMENT

Figure 1:
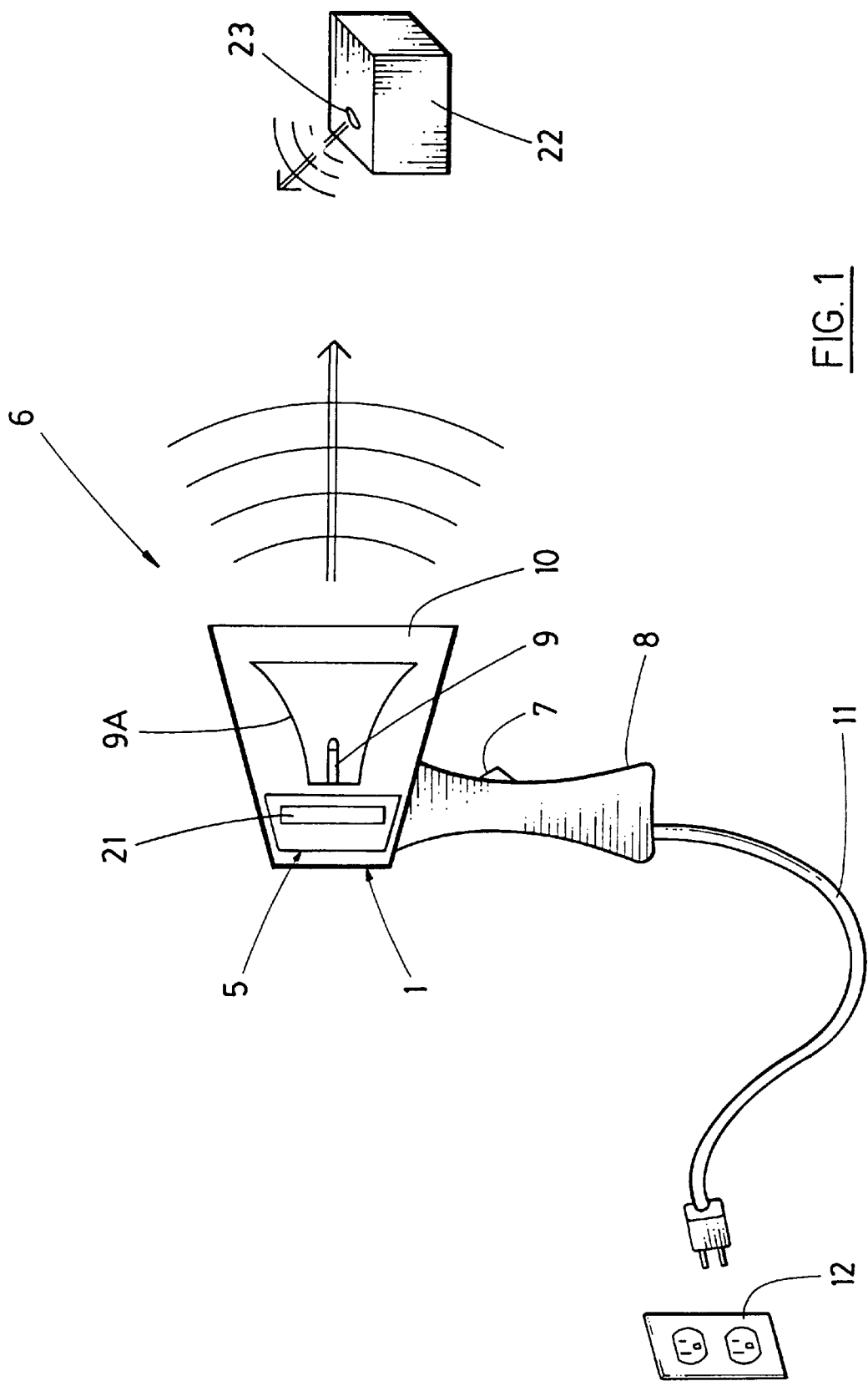
FIG. 1 is a diagrammatic side elevation view of a halogen lamp system according to a preferred embodiment of the invention when used in an automotive application.

Referring to FIG. 1, a lamp 1 contains a control unit 5. Together the lamp 1 and control unit 5 are a lamp system 6. The lamp 1 has a switch 7 on a handle 8. The lamp 1 also has a bulb 9 and reflector 9A. In this first preferred embodiment, the bulb 9 is a filament bulb 9, such as a tungsten halogen bulb 9. Halogen bulbs 9 give off a substantial amount of ultraviolet light without requiring a ballast. This allows the system 6 to be produced as a hand held model at a relatively inexpensive price.

Covering the bulb 9 is a filter 10. The filter 10, as is known in the art, allows the passage of incident light for the purpose of causing a chosen luminescent material to emit visible radiation at a substantially different wavelength than the incident light. The filter 10 limits the visible light incident from the lamp 1, other than that required to make the lumiescent material emit the different wavelength visible radiation. As will be discussed further below, the filter 10 limits visible light as much as is practical given limitations on cost and available technology. As will also be discussed further below, it is possible that an embodiment of the lamp 1 could be made without the use of the filter 10 provided phosphorescent properties are exploited. In this description the term "luminescent materials" is used to describe materials that are stimulated or excited by incident electromagnetic radiation of one wavelength, typically in the ultraviolet range, and return to their original state. As part of this process such materials emit visible light. In most cases the emitted radiation is of a substantially different wavelength from the incident radiation. The wavelengths are substantially different in the sense that an unaided eye can tell the difference between the different wavelengths. Certainly where the incident wavelength incident from the lamp 1 is invisible or barely visible ultraviolet light and the wavelength emitted from the luminescent material is visible light then the wavelengths will be substantially different.

In this description, luminescent materials include both fluorescent and phosphorescent materials. Fluorescent materials typically emit radiation within about 10 to the −8 power seconds after being stimulated, while phosphorescent materials emit after longer periods' up to hundreds of seconds. Luminescent materials are normally solids that are typically dissolved in solvents to create a solution for use in locating faults. The lamp 1 has a cord 11 which may be plugged into an AC source 12. The switch 7 may be a momentary switch 7 turning on the lamp 1 only when the switch 7 is held by an operator. This prevents the lamp 1 from being left activated when not in use.

The control unit 5 can convert the source voltage to a given voltage for the bulb 9 that is greater than the nominal rating of the bulb 9. This can increase the intensity of ultraviolet exciting or stimulating incident radiation for the same bulb 9. The increase in intensity of ultraviolet radiation is often greater than the increase in the intensity of the visible wavelength radiation emitted from the bulb 9.

The control unit 5 has a strobing circuit 21 that pulses the power from the power source 12 when the switch 7 is on. The pulsed power from the control unit 5 is available to the bulb 9 when the switch 7 is depressed. The bulb 9 pulses on and off in accordance with the timing of the pulsed power from the control unit 5.

In operation, the control unit 5 is connected to the power source 12. An operator grips the handle 8 and aims the lamp 1 at an object that is being tested, for example an automotive air conditioning component 22. The switch 7 is depressed and the bulb 9 is pulsed on and off by the strobing circuit 21. Luminescent material 23 in solution that is leaking from a fault in the component 22 absorbs the incident light and emits visible radiation that pulses. The emitted pulsing radiation stands out to allow the operator to see it.

Even though some visible light (outside of the wavelength required to cause the luminescent material to emit) is allowed to pass through the filter 10 (see the discussion regarding FIG. 2 below), the enhanced visibility of the material 23 is not to be underestimated.

The quality of phosphorescence, a substantially delayed emission of visible radiation, can further enhance the visibility of the pulsing emitted radiation from the material 23 as undesired incident visible light from the lamp 1 is extinguished while emission from the material 23 occurs afterwards. The delay between the cessation of the incident radiation and the cessation of the emitted radiation does not have to be lengthy, only enough to increase the chance that the user will see the emitted radiation. Delays in the order of 30 milliseconds or more would likely be sufficient to take advantage of this property as the human eye typically takes 30 milliseconds to register any change. Longer delays would be advantageous. It is recommended to select the phosphorescent material so that the emitted radiation from the material ceases sufficiently prior to the next pulse of the lamp 1 in order to more easily distinguish one pulse from the next. When a phosphorescent material is used for the material 23, it is possible that that filter 10 could allow the transmission of incident light of a wavelength that is not substantially different from that of the emitted light as the incident light will have extinguished when the emitted light is continuing to emit.

Care must be taken in selecting appropriate luminescent materials, particularly phosphorescent materials, for specific applications. Many luminescent materials are quite abrasive and their use in specific applications could be contraindicated, for example when used as an additive to components with moving parts.

Figure 2:
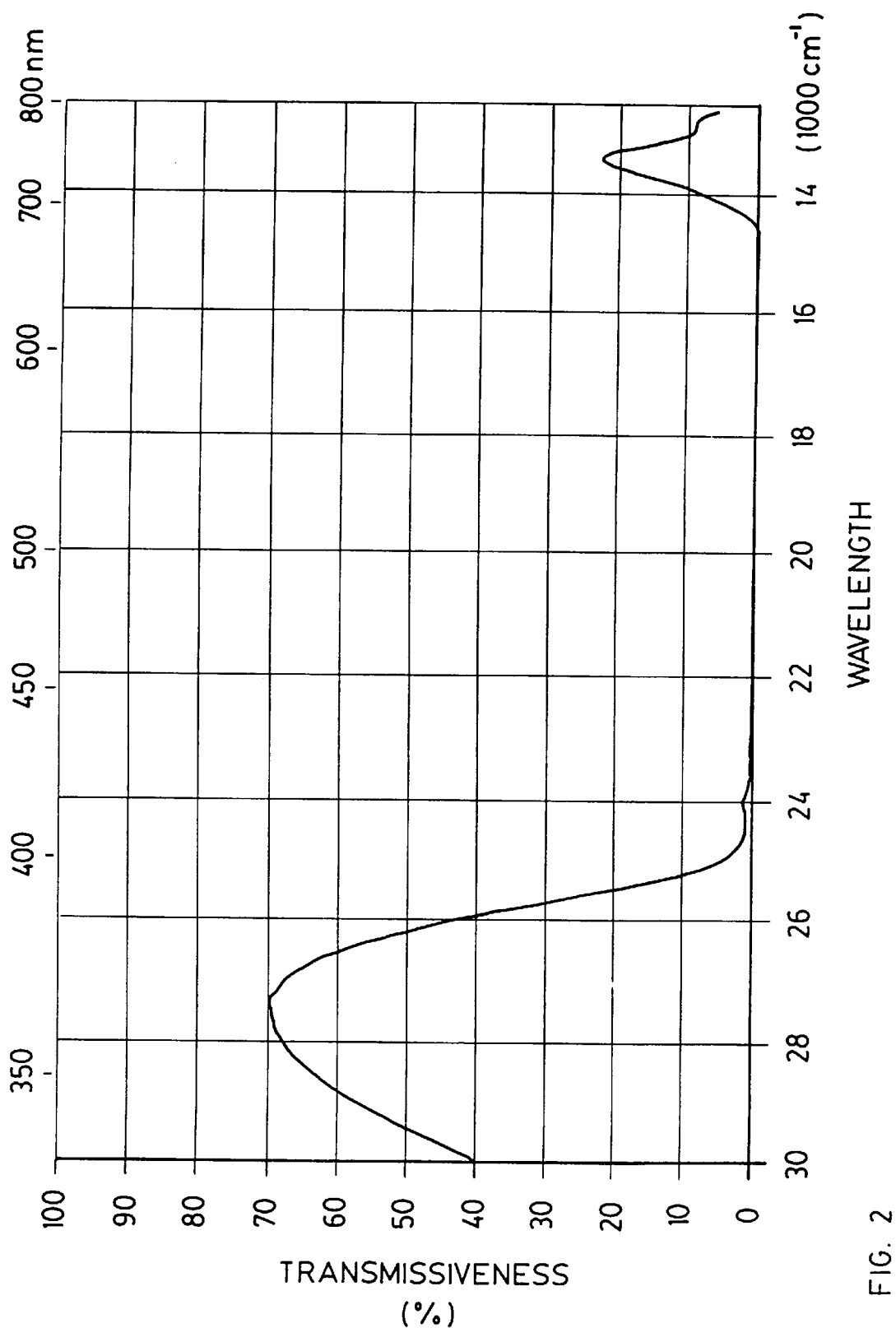
FIG. 2 is a graph of the light transmission characteristics of a filter employed in the lamp system of FIG. 1.

Referring to FIG. 2, as an example when the system 6 is to be used in conjunction with solvent yellow 43 fluorescent dye as the luminescent material, a Kopp™ No. 71 W filter 10 allows appropriate wavelengths of light to pass peaked at approximately 360 nanometers wavelength light, while limiting the amount of visible light emitted from the lamp 1 to almost nil. Solvent yellow 43 emits yellow light of approximately 530 to 600 nanometers wavelength under incident ultraviolet light of a wavelength of approximately 360 nanometers. Solvent yellow 43 is fluorescent, but not phosphorescent.

In FIG. 2, the horizontal axis is the wavelength of light incident from the bulb 9, while the vertical axis is the percent transmissiveness of the filter 10 at a given wavelength, The amount of filtering required for any particular application will depend on the relative amount of exciting or stimulating light generated from the bulb 9 versus the amount of visible light generated, particularly at or near enough to be confused with the wavelength of the emitted radiation from the luminescent material. The filter 10 is preferably selected to allow passage of the exciting or stimulating wavelength light while otherwise limiting visible light from the lamp 1.

The lamp 1 could also be used with luminescent materials that emit as a result of incident radiation of other wavelengths, including those in the visible spectrum, be selecting filter 10 appropriately to limit emission of incident visible light outside of that required to cause the material 23 to emit visible light. There are many luminescent materials that are excited by visible light and emit a substantially different wavelength visible light, including FITC that absorbs blue and emits green, and Texas Red that absorbs green and emits red. Luminescent materials that absorb non-visible light and emit visible light are preferred as the incident light does not detract from the visibility of the emitted visible light.

The bulb 9 can be pulsed at any frequency that tends to enhance the visibility of the emitted radiation. If the frequency is too low, the user may not notice the pulsing of the emitted radiation, particularly when the user is moving back and forth attempting to find it. If the frequency is too great then the pulse may tend to appear continuous, particularly if the bulb 9 does not extinguish quickly. A frequency of between 0.5 and 3 hertz is preferred for most users, although the principles described herein are not limited to that range. In the preferred embodiment, the bulb 9 was pulsed on for 0.5 seconds and left off for 0.5 seconds for a pulse frequency of 1 hertz and a pulse duration of 0.5 seconds.

As mentioned previously, when phosphorescent materials are used the emitted radiation from the material should cease sufficiently prior to the next pulse of the lamp 1 in order to distinguish one pulse from the next.

Additional benefits of the system 6 include reduced power consumption due to the use of pulsed rather than continuous power. It is possible to run the system 6 from a battery source 15 for reasonable working periods prior to recharging the battery source 15. Consequent modifications to the control unit 5 to run from low voltage DC power would be evident to a person skilled in the art.

In addition, when the bulb 9 is not running continuously the lamp 1 is cooler to the touch. This makes it safer to use. As well and as mentioned previously, it is advantageous to increase the amount of ultraviolet incident exciting or stimulating radiation generated by the bulb 9 by increasing the voltage at which the bulb 9 is driven. Increasing the voltage by 25% over nominal rating (for example, a driving a nominal 100 Volt bulb at 125 Volts) has been found to leave sufficient bulb life, while significantly increasing the intensity of ultraviolet exciting or stimulating radiation as compared to the increase in other wavelength incident radiation. This is due to the increased temperature at which the bulb 9 operates internally. The increased temperature can greatly reduce the life of the bulb 9; however, with pulsed use the bulb 9 is not activated for long periods and the reduction in life is less noticeable.

Figure 3:
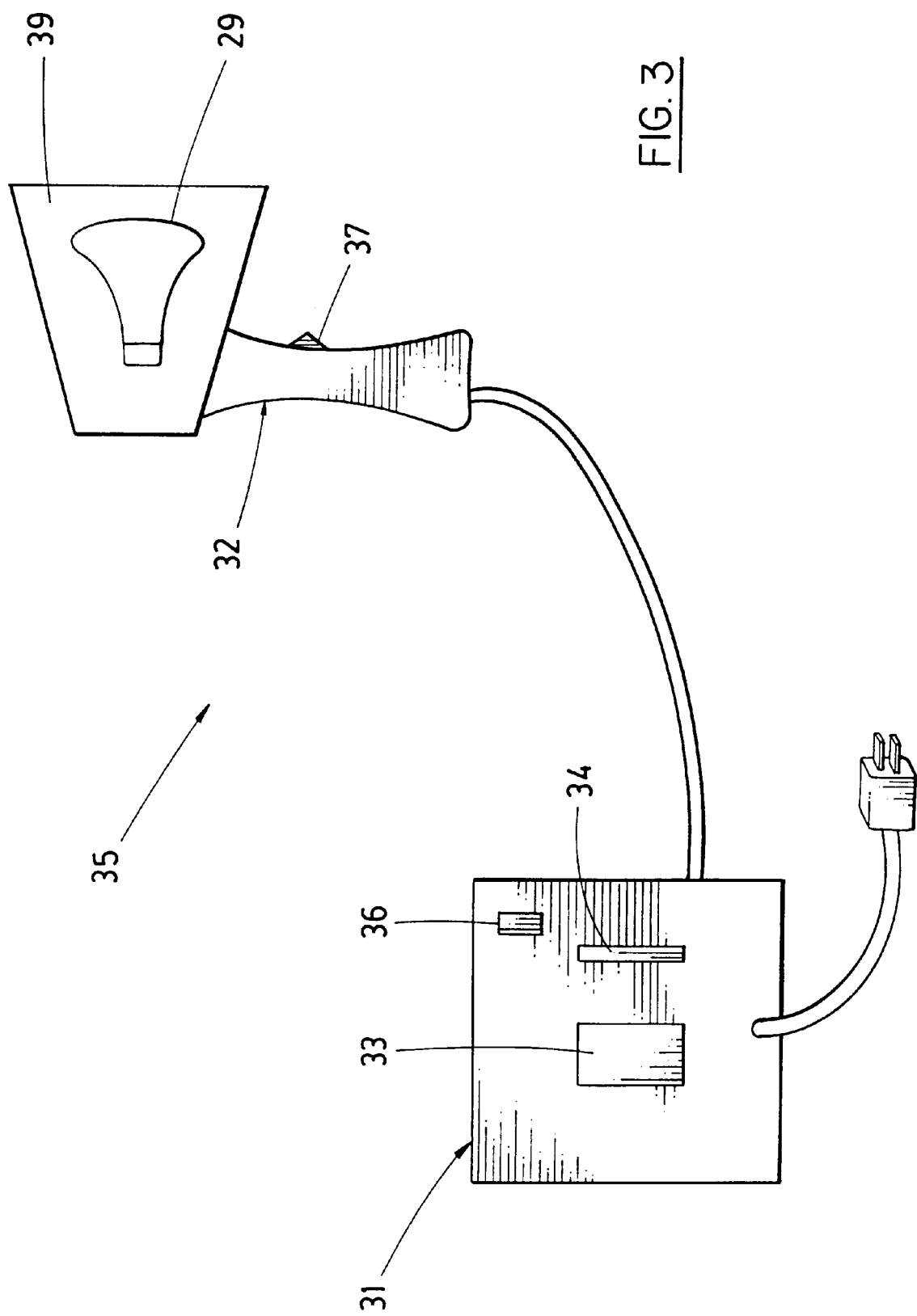
FIG. 3 is a diagrammatic side elevation view of a mercury vapour lamp system according to a preferred embodiment of the present invention.

Referring to FIG. 3, a further preferred embodiment uses a discharge bulb 29, such as a mercury vapour bulb 29, and a control unit 31 separated from lamp 32. The control unit 31 and the lamp 32 are separated because the control unit 31 uses a substantial mechanical ballast 33 that would make the lamp 32 too heavy for handheld use. The control unit 31 The bulb 29 does not have a fluorescent coating hat might otherwise be used where it is desirable to convert ultraviolet light from the bulb 9 to visible light.

The operation of the system 35 is similar to that of the system 6. The system 35 is turned on at a control switch 36. A momentary lamp switch 37 is depressed and the lamp 32 is aimed at an object to be tested. The strobing circuit 34 pulses the bulb 29 on and off, while a filter 39 limits visible light in a manner similar to the filter 10. Luminescent material on the object, if any, emits radiation that pulses on and off.

Although the mercury vapour lamp system 35 is generally more expensive to implement than the halogen lamp system 6, the system 35 tends to have a higher intensity of ultraviolet light.

It is possible to incorporate the control unit 31 into the lamp 32 so that the entire system 35 would be handheld and operate in a manner similar to the system 6; however, this requires an electronic ballast which is relatively expensive. It is also possible to use a discharge bulb 29 that is excited with RF electronic energy and does not require a ballast 33. This simplifies the control unit 31 and reduces expense in manufacturing.

Figure 4:
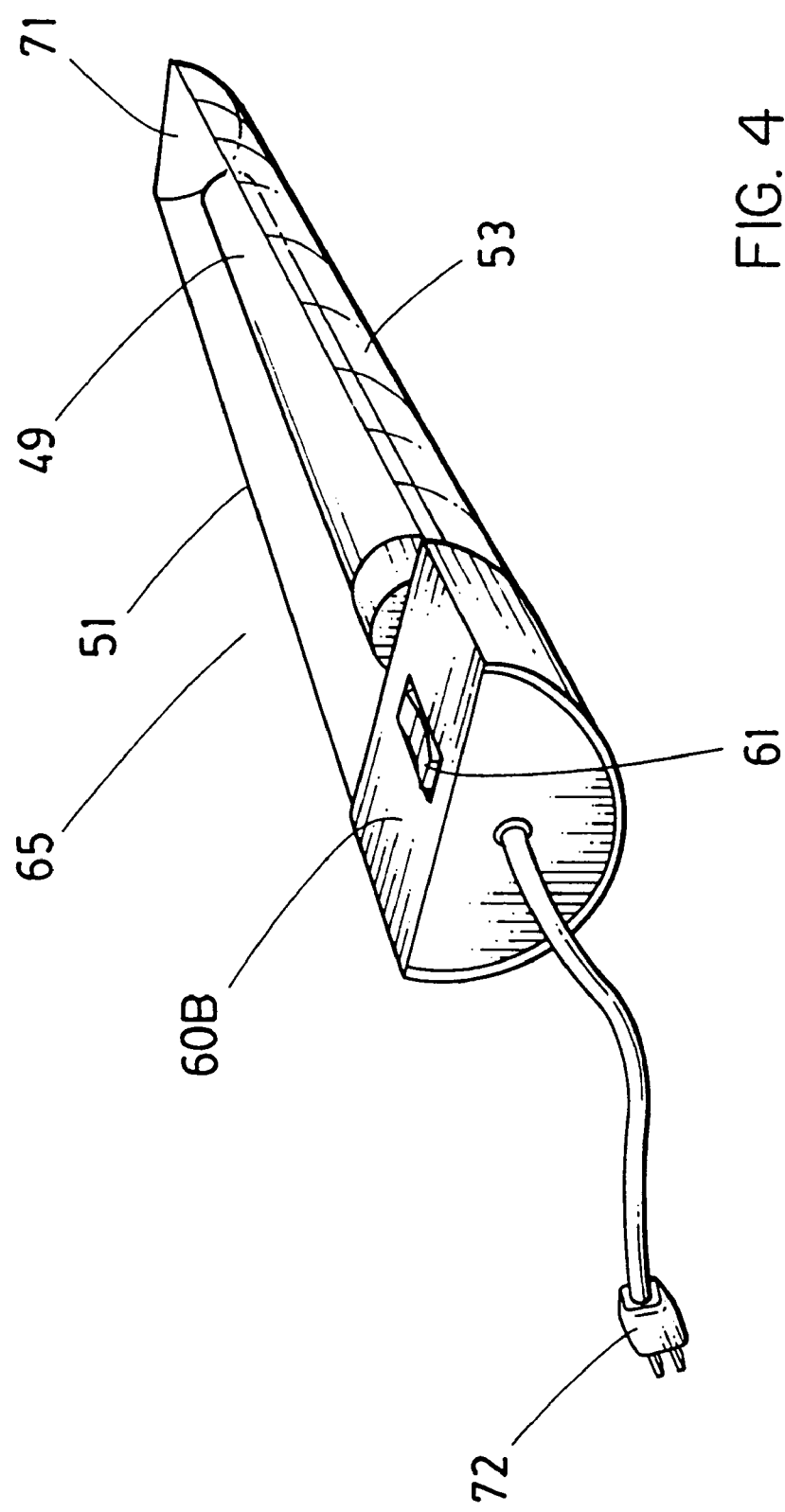
FIG. 4 is a perspective view of a fluorescent lamp system according to a preferred embodiment of the present invention.
Figure 5:
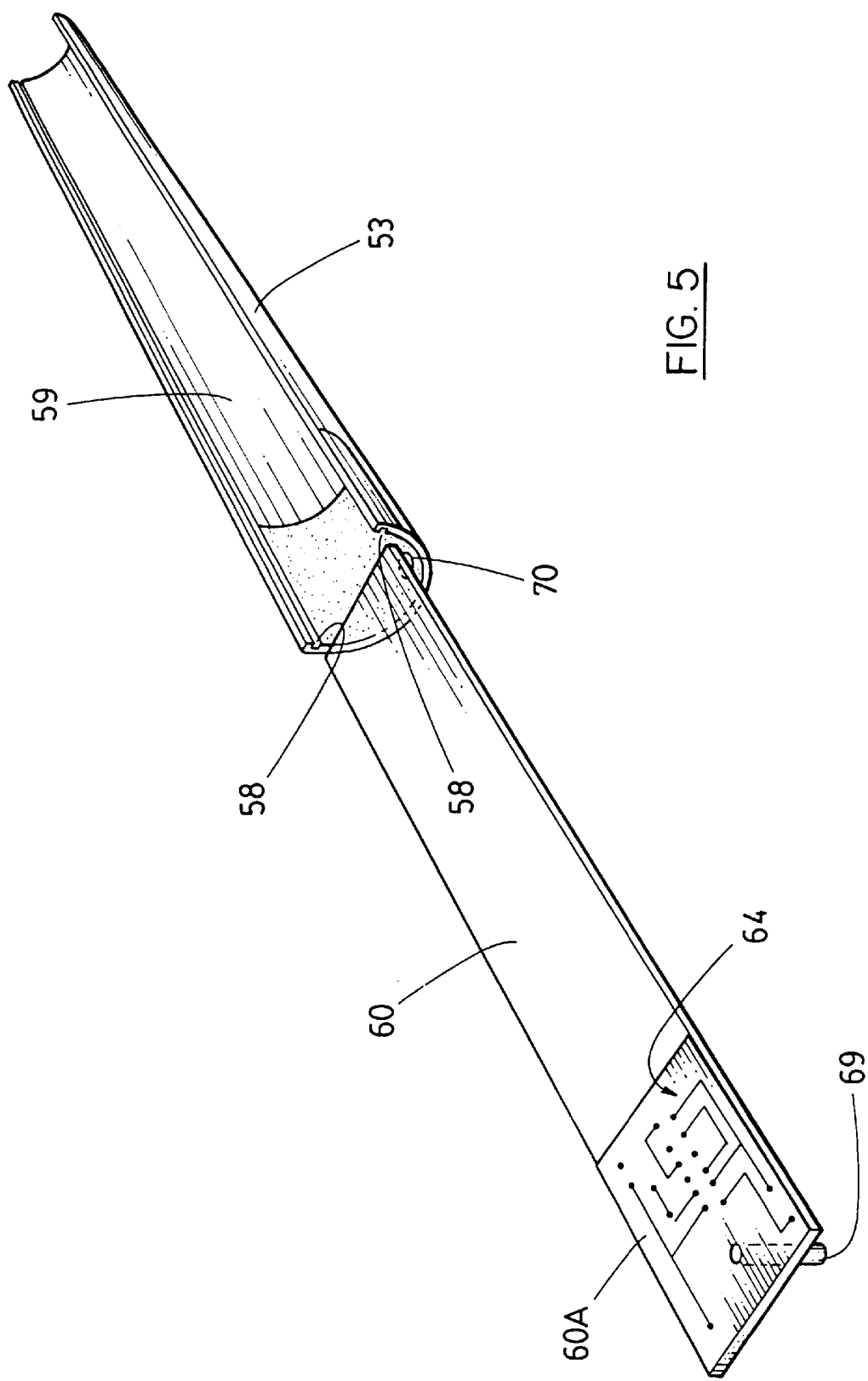
FIG. 5 is an exploded perspective view of certain components of the fluorescent lamp system of FIG. 4.
Figure 7:
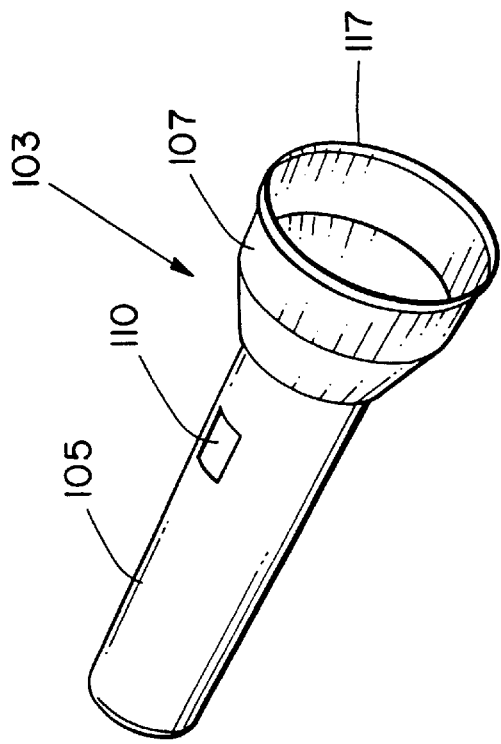
FIG. 7 is a perspective view of a casing used in the lamp system of FIG. 6.
Figure 6:
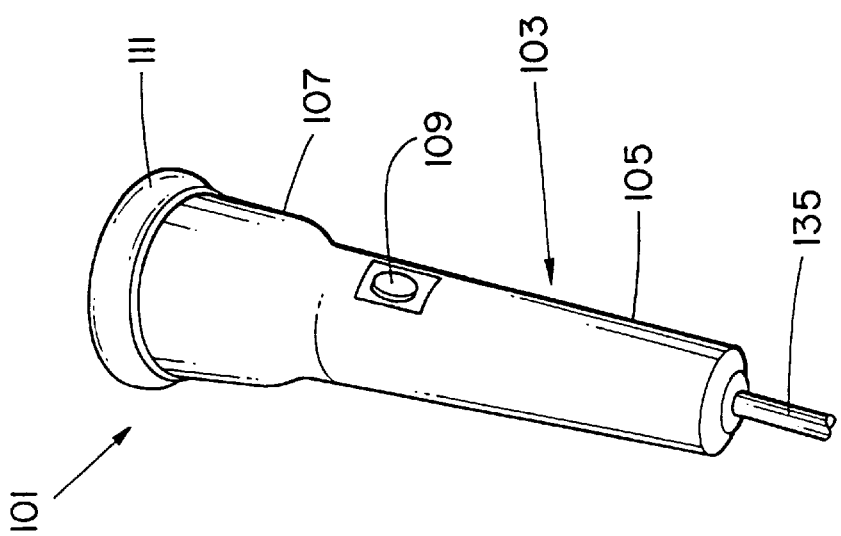
FIG. 6 is a perspective view of a lamp system according to a preferred embodiment of the present invention.
Figure 8:
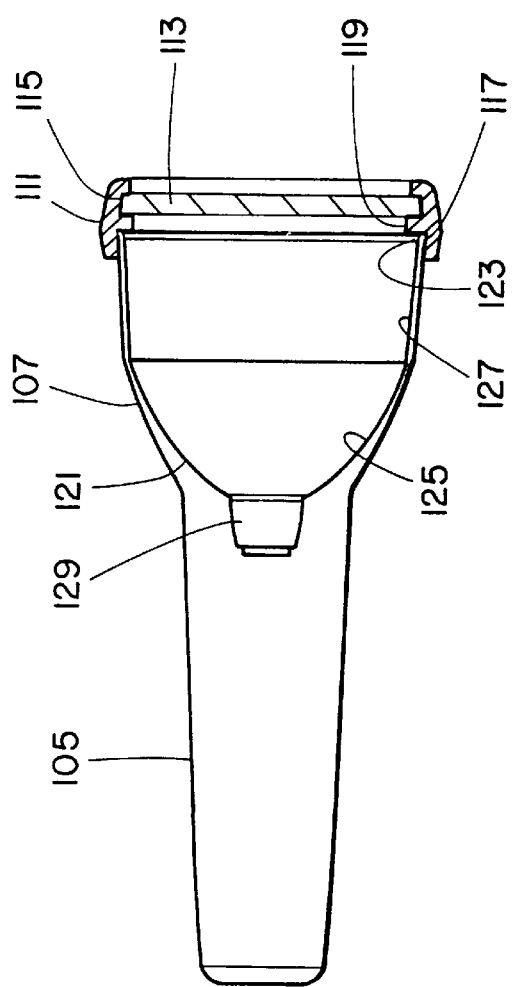
FIG. 8 is a side view of a lamp system of FIG. 6.
Figure 9:
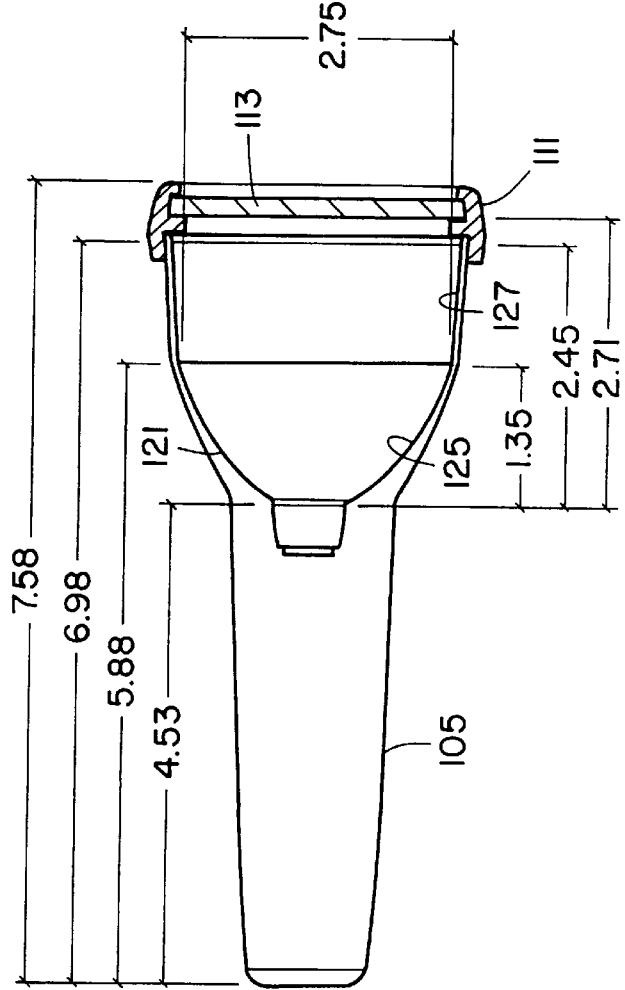
FIG. 9 is a cross-section of the lamp system of FIG. 8.
Figure 10:
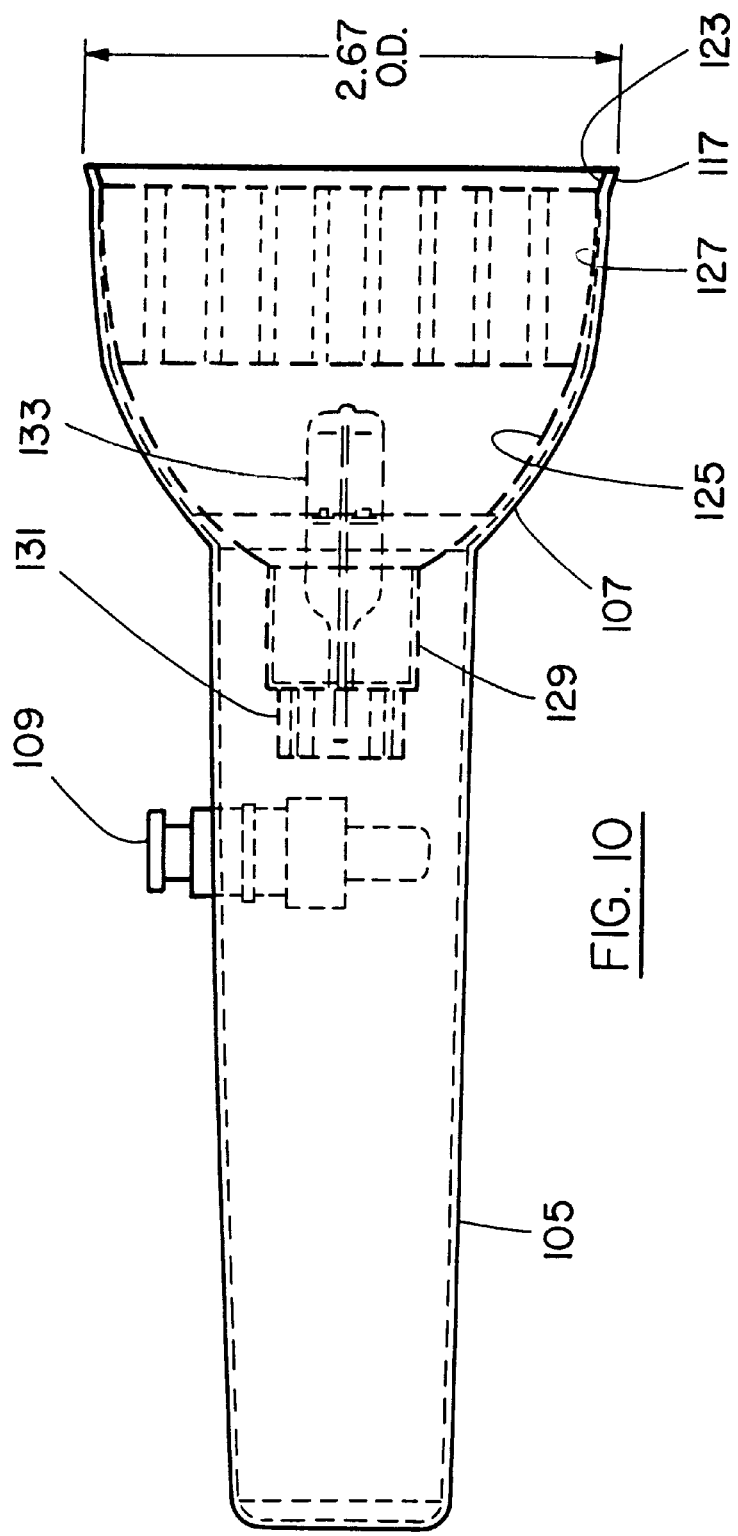
FIG. 10 is a cross-section of the lamp system of FIG. 6, showing a bulb, socket and switch.

Referring to FIG. 4, a further embodiment uses a fluorescent bulb 49 in a fluorescent lamp 51. The lamp 51 has a wand shape and is particularly useful in tight spaces. As shown in FIG. 5, a back casing 53 has a U-shaped cross-section with opposing slots 58 along either side of the U. The back casing 53 is opaque and the a substantial portion of the interior is coated with a reflective material 59. The slots 58 hold a transmissive shield 60 over the fluorescent bulb 49.

One end of the shield 60 forms a printed circuit board 60A. The reflective material 59 need not extend across the casing under the board 60A.

The portion of the casing 53 surrounding the board 60A is enclosed by a housing 60B. The housing 60B holds a three way toggle switch 61 for ON STEADY—OFF—ON STROBING. The board 60A holds a DC inverter and a strobing circuit. The DC inverter converts from DC to AC power for use by the fluorescent bulb 49, while the strobing circuit pulses that power on and off to the fluorescent bulb 49. The components of the board 60A form a control unit 64. The lamp 51 and control unit 64 form an integral fluorescent lamp system 65.

A simple method for fixing the board 60A, casing 53 and housing 60B is to create them from injection moulded plastic with a boss 69 extending from the circuit board 60A above a hole 70 in the casing 53. A corresponding hole, not shown, appears in the housing 60B, the housing is placed over the casing and a screw, not shown extends through the respective holes in the housing 60B and the casing 53 into the boss 69. A cap 71 encloses the end of the casing opposite the housing 60B. The back casing 53 should extend beyond the shield 60 in order to distance the shield 60 from debris that may be on a bench or other work area where the lamp system 65 is placed.

A plug 72 is provided for connection to a DC source, for example a waist mounted DC battery pack, not shown.

The bulb 49 may be either a black light (BL) or a blacklight blue (BLB) fluorescent bulb 49 selected to emit increased amounts of ultraviolet radiation if the system 65 is to be used in conjunction with a luminescent material that emits under ultraviolet incident light. As a BLB bulb 49 is selected to emit primarily non-visible wavelengths of an ultraviolet frequency, the shield 60 may be clear or even made from a wire mesh or protective material, as long as it is ultraviolet transmissive, In this case the shield 60 is provided primarily to protect the bulb 49 from damage and to keep the bulb 49 clean. If the bulb 49 is a BL bulb 49 then the shield 60 will also need to filter light in a manner similar to that of the filters 10, 39. Other fluorescent bulbs 49 having differing spectrums may be used where they have sufficient intensity in a given wavelength that is required for incident light.

In operation, the lamp 51 is put into a strobing mode by switching to ON STROBING at the switch 61. The DC inverter converts power from the plug 72 to alternating current, while the strobing circuit pulses that power to the bulb 49. The lamp 51 is shone near to a body, and luminescent material on the body, if any, is illuminated and emits visible radiation that pulses on and off.

The system 65 is designed to be a low cost, low power consumption alternative to the systems 6, 35. In most cases it will be desirable to simply operate from a fixed voltage DC source. However, the lamp system 65 can be used with AC power by replacing the DC inverter with an AC ballast. Alternatively, the system could be provided with a DC inverter/AC ballast connected to a voltage switch for selected frequencies and voltage, for example DC 12 volts and AC 120 V 60 Hz, or for automatic sensing. The plug 72 could be adapted for various outlets or terminals.

Fluorescent bulbs 49 have a relatively low intensity. The pulsing on and off of the emitted radiation is particularly useful to enhance what is otherwise a relatively low intensity of emitted radiation. It is also useful to overdrive the bulb 49 as described for the lamp system 6 for the generation of higher intensity emitted radiation.

Each lamp system 6, 35 or 65 can be sold as a kit along with the luminescent material that matches the particular radiation incident from the system 6, 35 or 65. Alternatively, each lamp system 6, 35 or 65 may be sold separate from corresponding luminescent material for later combination into a kit and use by a user.

As is evident from the different embodiments described above, the principles of the invention are not limited to any one bulb type or control system configuration. For example, a laser light source could be used with appropriate luminescent materials to provide a high intensity of specific wavelength incident radiation.

Referring to the FIGS. 6 through 18, a fault locating lamp system 101 as a casing 103 with a handle 105 at one end and a flared lamp housing 107 at an opposing end. A button switch 109 is provided through a slot 110 in the handle 105. The switch 109 could be a slide switch or other on/off device, not shown.

About the housing 107 is a rubber lens ring 111 that retains a circular filter lens 113 (see FIG. 8) in a groove 115. The ring 111 attaches the housing 107 by stretch fit, A flare 117 on the housing 107 assists in retaining the ring 111. The ring 111 has an annular flange 119 that separates the housing 107 from the lens 113.

A reflector 121 rests within the housing 107. The reflector 121 has a flare 123 corresponding to the flare 117. The two flares 117 and 123 fit together to prevent the reflector 121 from slipping further into the housing and maintain the outside of the two flares 117 and 123 substantially flush and in contact with the flange 119. This prevents the reflector 121 from slipping out of the housing 107. It also maintains the reflector 121 in a generally fixed position within the housing 107.

The reflector 121 has a reflecting section 125, an elongate spacing section 127 and a neck 129. The neck 129 fits around a bulb socket 131. A bulb 133 fits within the socket 131. The reflector section 125 can have the dimensions shown in FIG. 14; so, that a tungsten halogen lamp having the form factor shown in FIG. 17 will direct light from the bulb 133 generally straight out of the housing 107. An example of a bulb 133 that would work with a reflector section 125 as shown in FIG. 14 is an OSRAM HLX 64610 50 watt 12 volt lamp. he curvature of reflecting section 125 is either a parabola to obtain a spot of light at a great distance or a long focal length ellipse to obtain a spot of light at a finite distance. The values listed in FIG. 14 are the values for an ellipse which focuses the light 18 inches in front of the reflector 121. As the desired focal distance increases to infinity this elliptical curve will change to a longer focal length ellipse and finally to a parabola.

A standard reflector finish is the "Alzak" (Alcoa Trademark) process which protects the aluminum reflector surface with an anodic coating. This coating however is not optimal as it absorbs UV energy rather than reflecting it. The reflector 121 can be made of aluminum or plastic and the preferred finish is a vapor deposit of aluminum and a protective coating of silicone oxide (SiO) or silicone dioxide ($SiO_2$). This coating passes almost all of the UV energy.

The spacing section 127 provides some distance between the lens 113 and the bulb 133 to lessen the potential for heat related stress cracking of the lens 113 and lower heat build-up on the lens 113. With higher heat bulbs, such as a 50 W halogen bulb, it may be advisable to use thermoset or other suitable high temperature plastic material for the casing 103. Similarly, the rubber ring 111 may need to be made from a high temperature material. A power wire 135 extends from the handle 105. The wire 135 is connected to the bulb 133 through the switch 109. The power wire is connected to a 12V DC source, not shown, such as an automotive battery. The system 101 can equally be connected to an alternative DC or AC source with commensurate modification to the bulb, or the addition of control circuitry within the system 101 to convert the source power to 12V DC. The reflector 121 may be formed from aluminum with an aluminum coating that is in turn coated with a protective coating for ultraviolet enhanced reflection, such as silicon oxide or silicon dioxide.

The lens 113 is an isotropic dichroic filter, The lens 113 transmits some light, while reflecting other light back into the housing 107. Minimal amounts of light are absorbed by the filter. Most fluorescent materials used in leak detection and NDT fluoresce under ultraviolet A light (UV A 350 to 400 nm), preferably peaked at 365 nm. UV B 280–320 nm and UV C 200–280 nm are undesirable and are to be filtered out if possible.

Figure 12A:
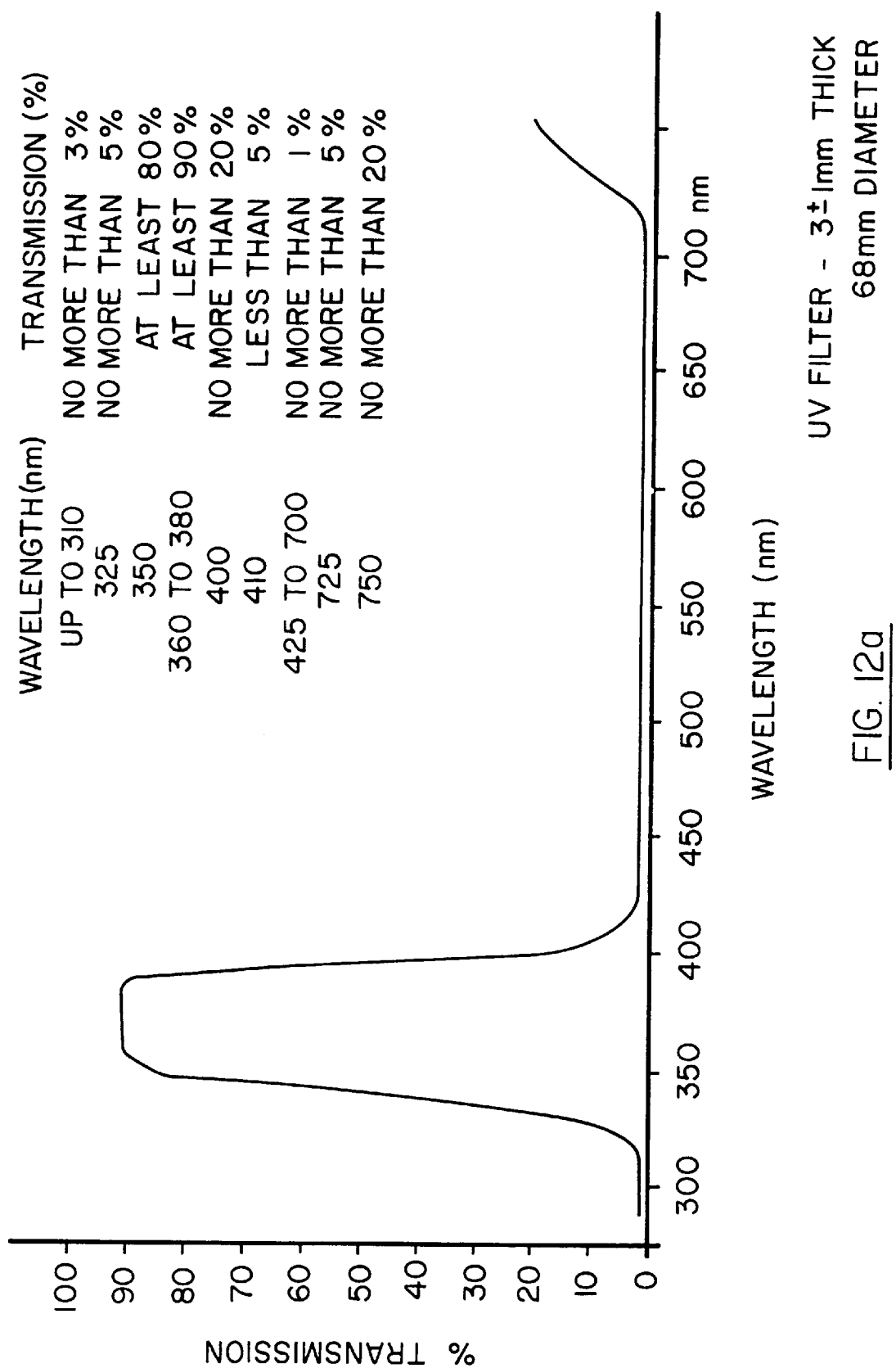
Figure 12B:
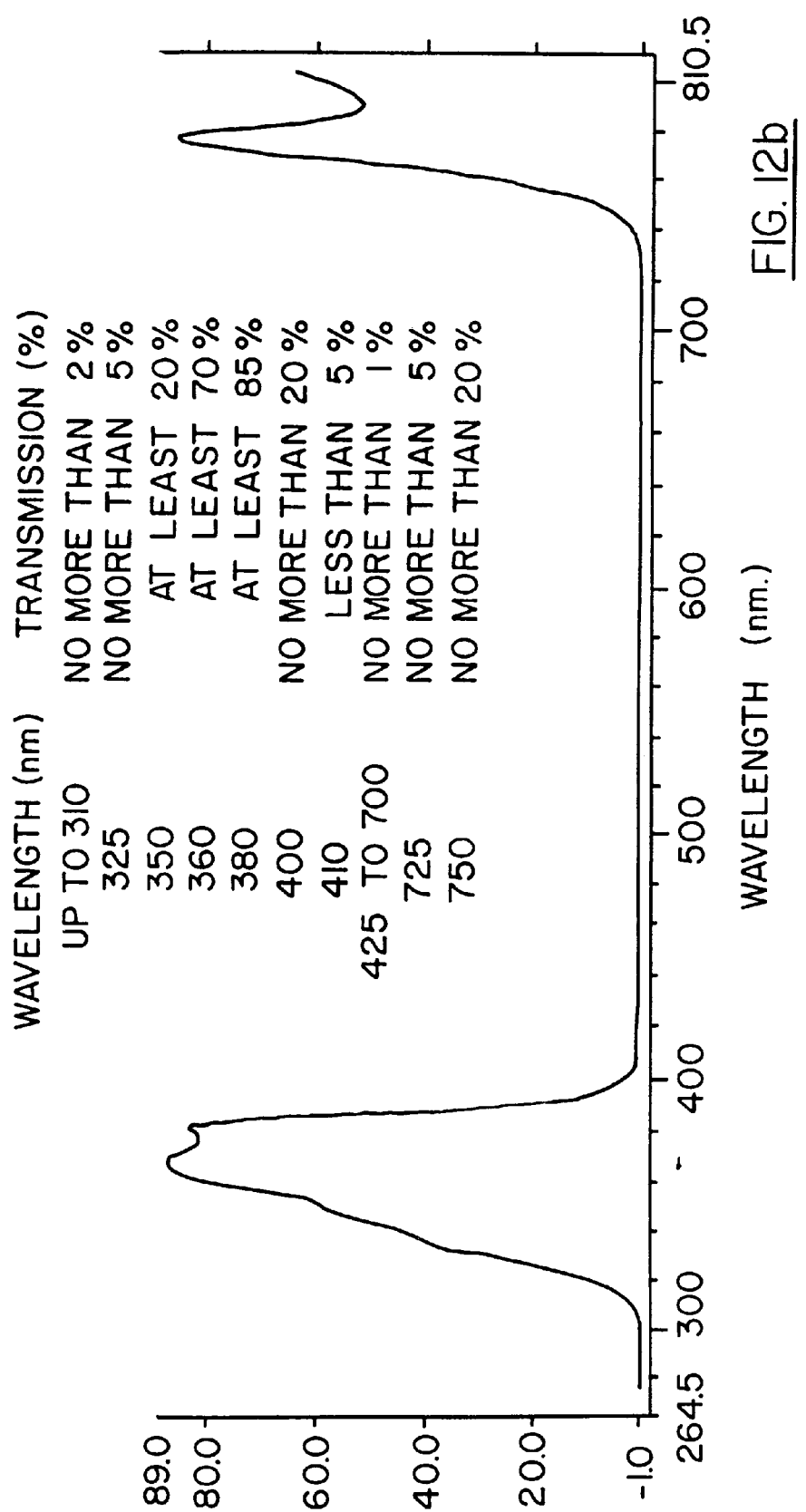
Figure 18:
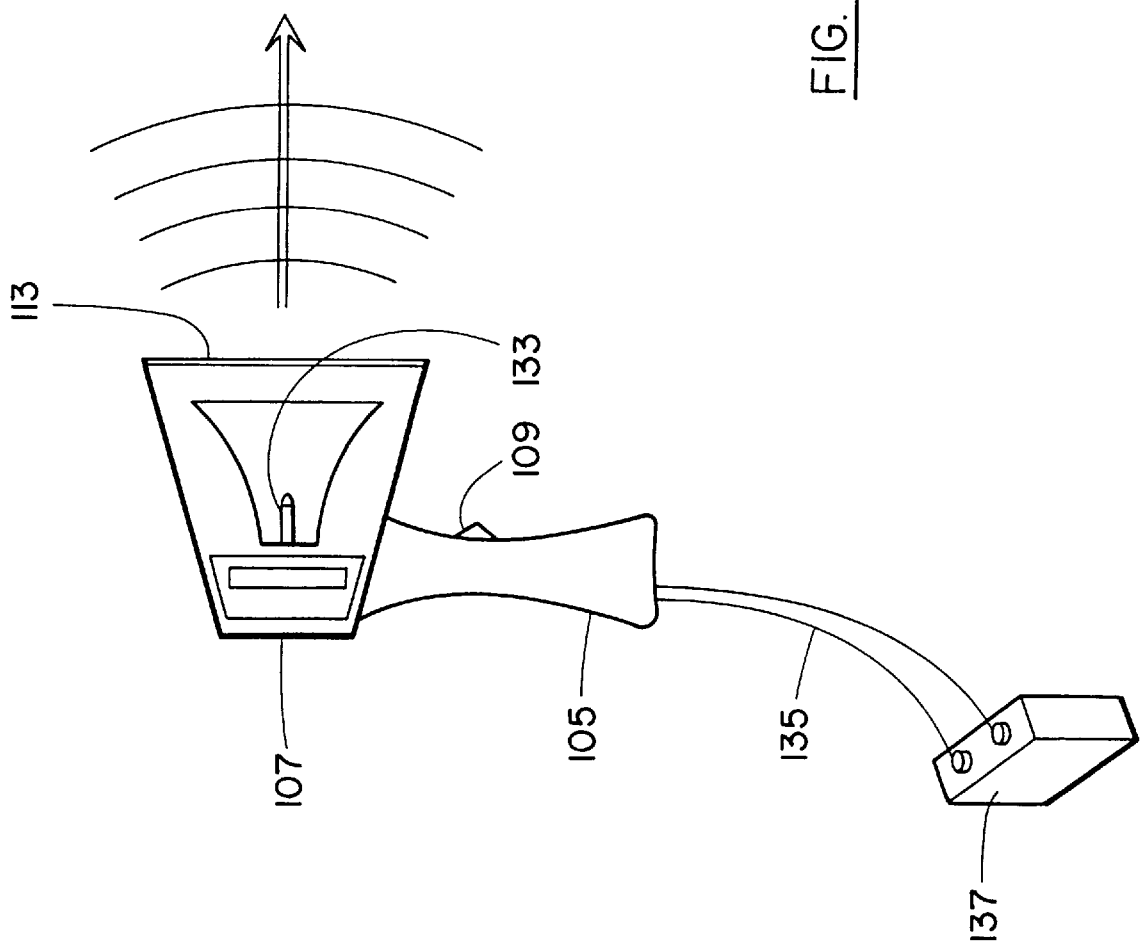
FIG. 18 is a perspective of an alternative system, employed in testing a body and powered by a battery.
Figure 19:
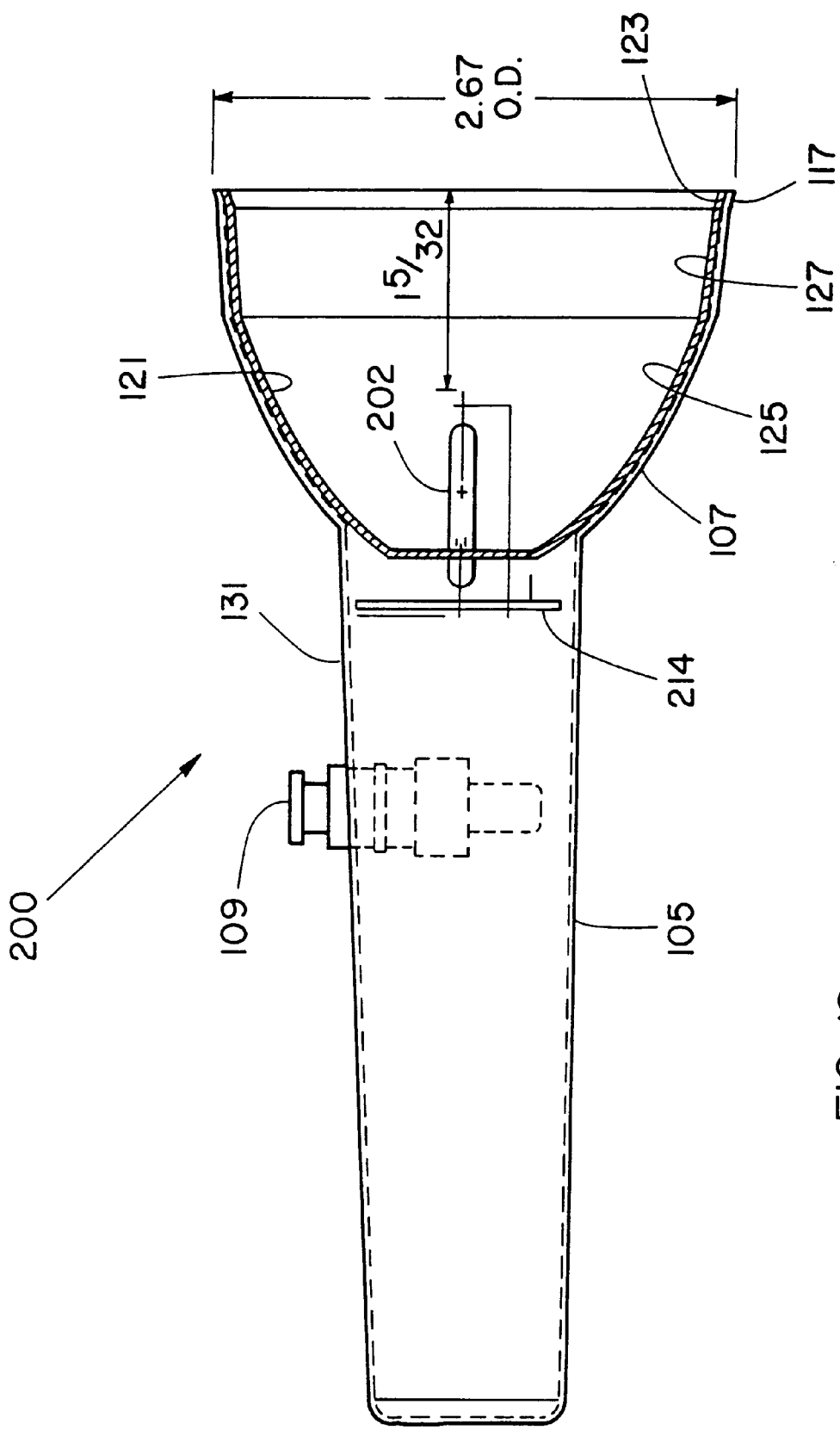
FIG. 19 is a cross-section of a lamp system according to an alternative preferred embodiment of the present invention.
Figure 20:
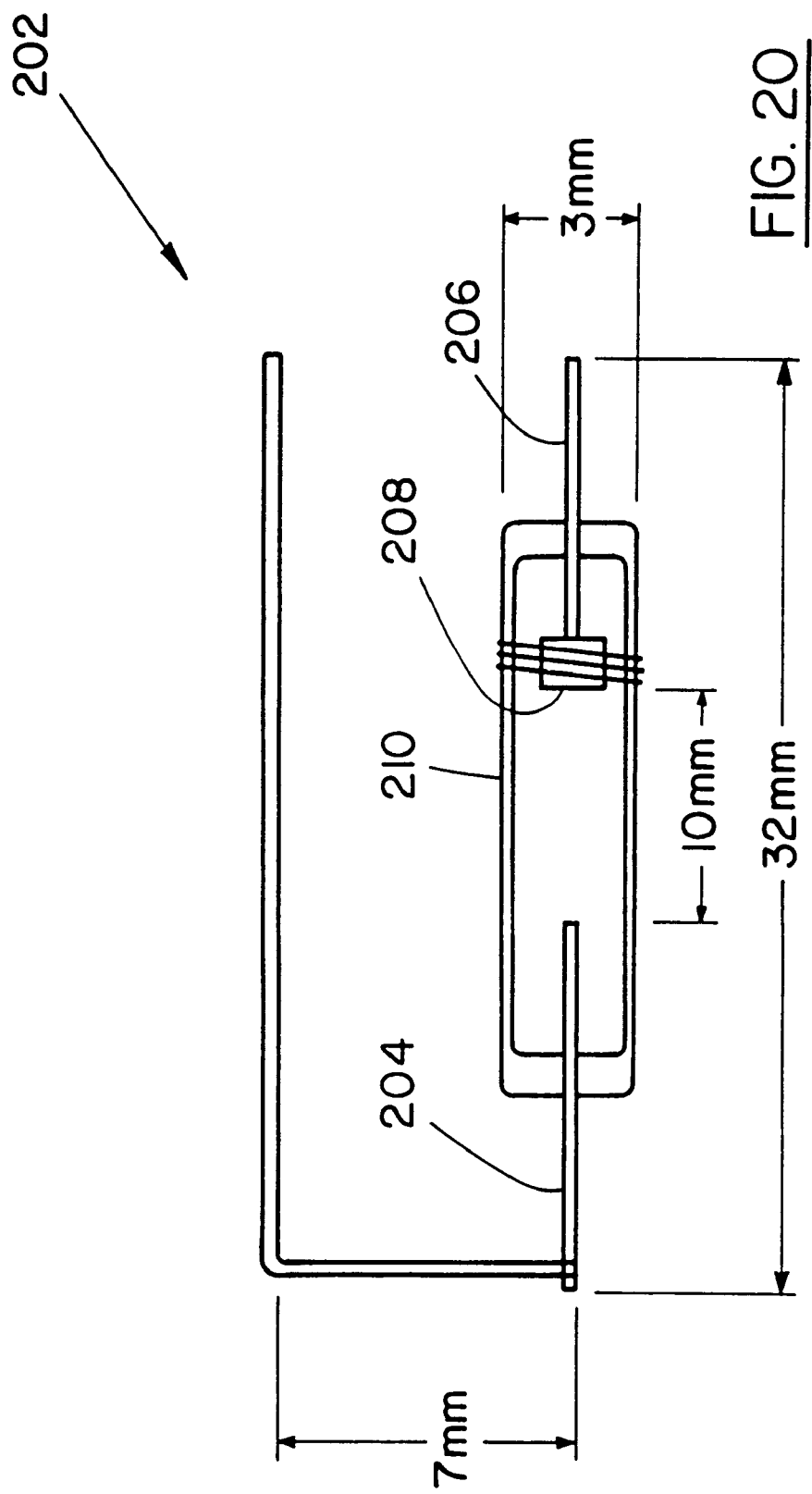
FIG. 20 is a cross-section of a flashtube employed in the system of FIG. 19.

A desired transmission curve for the lens 113 is shown in FIG. 12*a*. The lens 13 has an ultraviolet/visible light passband of approximately 325 nm to 410 nm with a peak including 365 nm. Dichroic filters are formed by depositing multiple layers of thin films on one or both sides of the lens 113. The cost of the lens 113 will depend upon the technique used to create the lens, the materials used, the number of layers required and whether the deposition is on one or two sides of the lens. The curve of FIG. 12a can be modified to balance the price point of a particular system 101. For example, the curve of FIG. 12b may provide a more practical specification for a less expensive lens 113. It may also be acceptable to have limited amounts of blue or red light transmitted through the lens 113 in order to reduce the cost of the lens 113. This will depend on the intended application for the system 101.

A sample filter that can provide the transmission characteristics required by some applications for the lens 113 is an Automated Entertainment (Burbank, Calif.) HD Dichroic UV Pass Blacklite™ Filter.

A dichroic lens 113 can provide 80% or greater ultraviolet transmissiveness. The high ultraviolet transmissiveness allows the bulb 133 to be a halogen tungsten bulb 133, while still providing sufficient UV light for many desired NDT and leak detection applications. Although a tungsten halogen bulb provides many additional benefits, such as instant on and relatively low price, it is not required that the bulb 133 be a tungsten halogen bulb in order to obtain high ultraviolet transmissiveness from the lens 113. The lens 113 could be used with mercury vapour and other bulbs 133.

The dichroic lens 113 can also provide less than 1% visible light transmissiveness; so that, systems 101 can be produced for use in NDT. This feature, although not currently required by any specification for leak detection, is also advantageous when systems 101 are used for leak detection.

The lens 113 can also run cooler than prior art absorption lenses, not shown, because the reflected light is driven away from the lens 113 and not retained by it. The components of the system 101 will need to be designed to withstand any additional heat retained by the system 101 as a result of the reflected light. It is possible that heat savings through the increased ultraviolet transmissiveness of the lens 113 may compensate for a significant portion of the heat retained by reflection from the lens 113 back into the housing 107.

In operation, the system 101 is connected at the wire 135 to an automotive 12V DC battery 137. The system 101 is hand-held at the handle 103 by an operator. The switch 109 is depressed to power the bulb 133. The bulb 133 illuminates and light emanates from the bulb 133. The lens 113 reflects that transmits a portion of the light and reflects substantially all of the remainder.

The lens will absorb some light; however, this is a relatively small amount of the overall light that hits the lens 113. As previously discussed, the actual transmissiveness curve for a particular lens 113, and thus the percentage of visible versus invisible light reflected and transmitted, will depend on the particular application. A transmissiveness curve for the lens 113 as shown in FIG. 12 will be useful for a wide variety of NDT and leak detection applications.

The operator directs the system 101; so that, the transmitted light is directed at a body 139 to be tested, for example an aircraft wing 141. NDT is used to identify possible stress fractures or other such faults in the wing 141. Fluorescent dye mixed with magnetic particles produced a distinctive pattern in the area of the fault. Ultraviolet light from the system 101 will cause the dye to fluoresce and reveal the pattern. This identifies the location of the stress fracture, or fault.

Alternatively, the body could be an air conditioning unit or other device to be tested, not shown. The testing of an air conditioning unit involves the introduction of fluorescent dye mixed with refrigerant oil. The dye leaks out of the unit and fluoresces when light from the system 101 is shown on the unit. This identifies the location of the leak, or fault, in the unit. Further detail on leak detection is described in the previously mentioned co-pending patent application of one of the inventors.

A control unit, not shown, could be employed in the system 101 to cause the bulb 133 to flash. As described previously, such flashing can provide additional assistance to the operator of the system 101 in locating the fluorescent dye and revealing the fault.

A dichroic lens 113 which blocks all or substantially all of the visible light from passing through the lens 113 will provide increased effectiveness for a flashing lamp. As mentioned in the co-pending application, the flashing of ultraviolet light increases the visibility of the fluorescing dye; however, the co-existence of flashing visible light can detract somewhat from the benefit of the flashing ultraviolet light. When substantially all of the visible light is blocked, only the flashing of the fluorescent material remains. This is very useful in locating the dye.

As mentioned previously, a halogen bulb 133 is particularly useful for the system 1 when used in flashing applications as it has virtually instant on/instant off characteristics without further modifications.

The control unit could also provide for overdriving of the bulb 133 beyond the bulb's normal power and voltage ratings in order to generate higher amounts of ultraviolet light from the bulb 133. These techniques are also described in the co-pending application mentioned previously.

The lens 113 as shown in FIG. 4 has a flat profile. It is possible to make lenses 113 having other profiles, example of which is shown in FIG. 11b. The lens 113 of FIG. 11b has a maximum deflection of ⅜"; so that, the ring 111 provides some protection to the lens 113 from bumps and scratches.

The system 101 has a D battery handheld flashlight-type profile. It could also have another profile, handheld or otherwise. It may be desirable to use a hand-held lamp system 101 having the style depicted in FIG. 18, particularly if the system 101 is to be used in conjunction with a mercury vapour lamp that generates a great deal of heat. It may be desirable for continuous testing to have the system 1 mounted on a stand or other mounting, not shown.

The halogen bulb 133 used in a D battery flashlight profile was 50 w. The casing for the D battery profile is preferably made from thermoset plastic to avoid melting at higher temperatures resulting from the compact configuration.

The possible increased ultraviolet efficiency of the system 101 can result in a significantly smaller form factor. As shown in FIG. 11c, the diameter of the lens 113 is only 2¹¹⁄₁₆" This is very useful in tight spaces. It is also helpful in decreasing the size and weight of the tools that an operator needs to carry. As well, the system 101 can have lower power consumption. This is particularly helpful for battery powered applications. It can also result in lower operating temperatures.

Other than emission of light through the lens 113, the casing 103, button 109 and ring 111 do not allow light to escape from the system 101.

Figure 21:
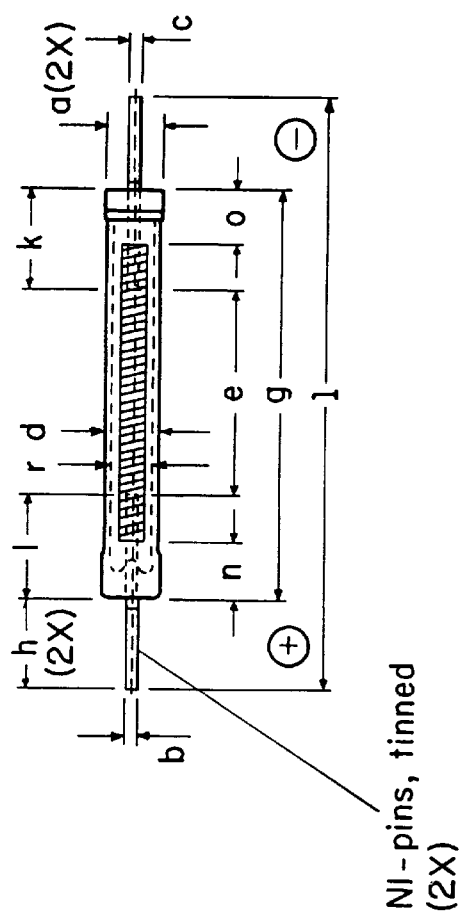
FIG. 21 is a detailed cross-section of the flashtube of FIG. 20 showing mechanical data, FIG. 22 provides operating data for the flashtube of FIG. 20.
Figure 23:
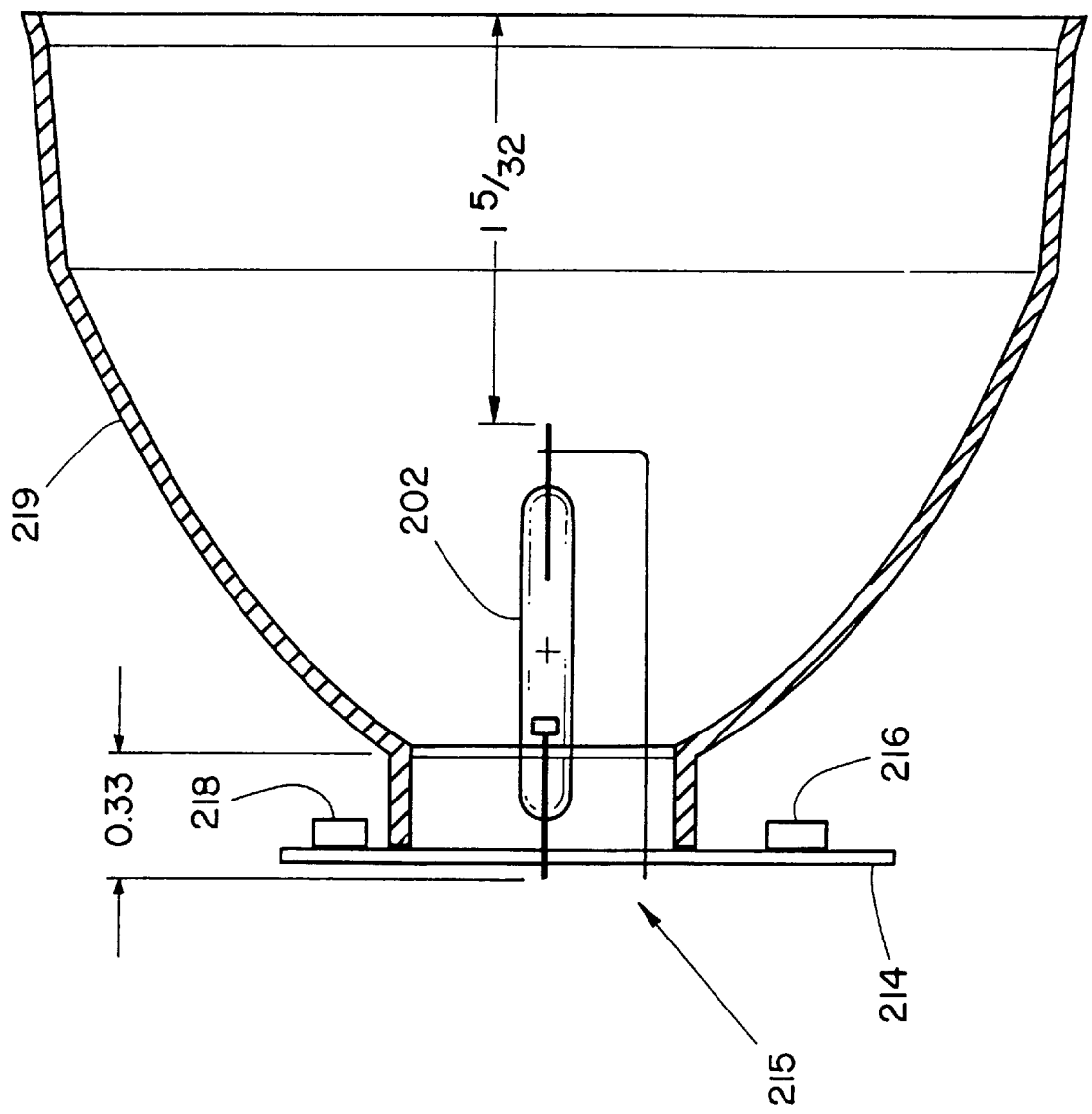
FIG. 23 is a cross-section of a reflector and control unit employed in the system of FIG. 20.

In an alternate embodiment, a system 200 may incorporate a high pressure arc lamp electronic flashtube 202 in place of the bulb 133, An example of a suitable flashtube 202 is a Xenon flashtube AGA0210 from Heimann of 221 Commerce Drive, Mongomeryvile, Pa. 18938 (phone 215-365-0700) having the mechanical data and operating data shown in FIGS. 21 and 22.

A flashtube 202 consists of a cathode 204, anode 206, trigger electrode 208 and glass tube 210 partially enclosing the cathode 204 and anode 206 to provide an arc length e. The glass tube 110 is filled with Xenon gas.

Figure 25:
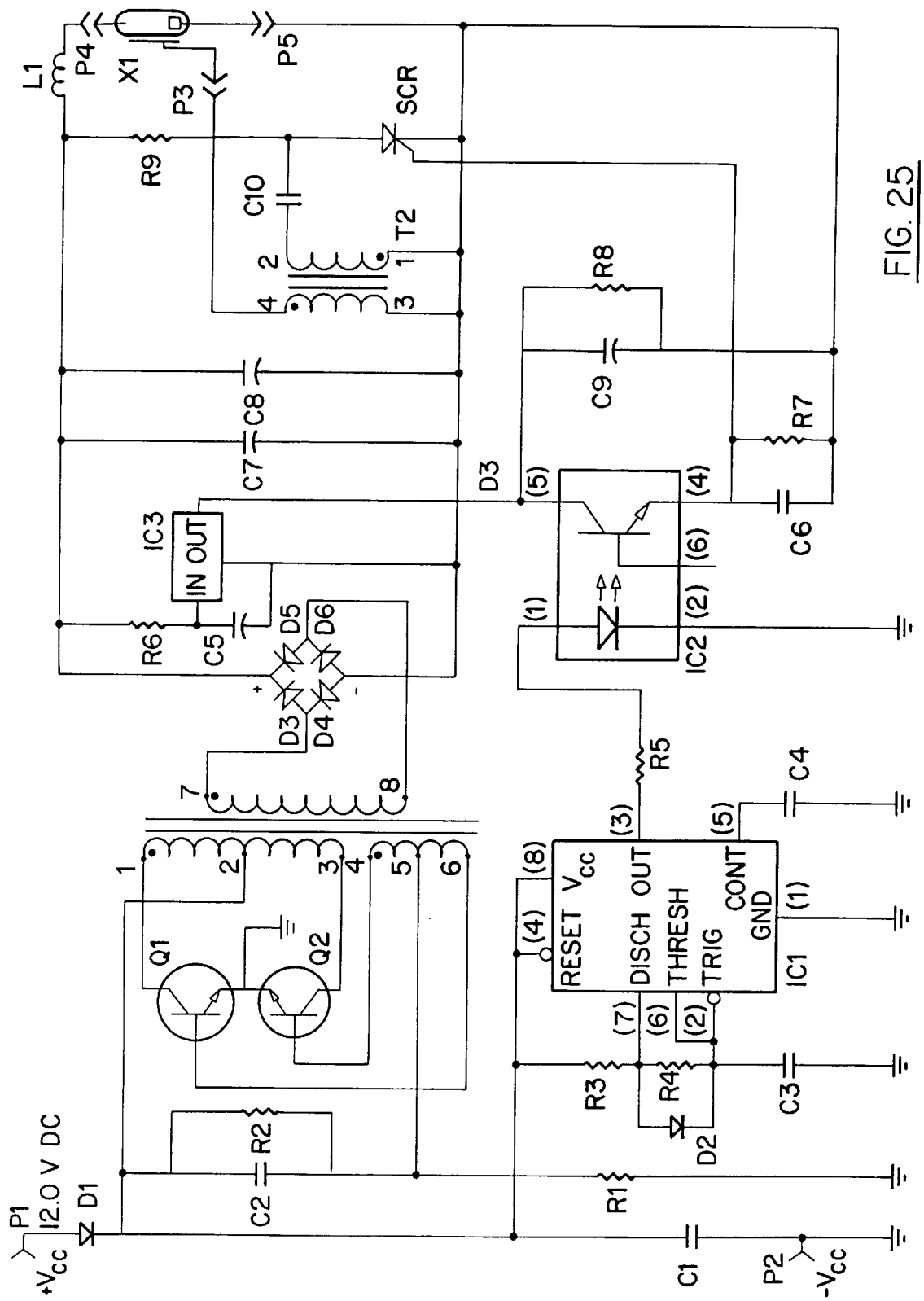
FIG. 25 is an example of a circuit diagram of the control unit of FIGS. 20 and 23.
Figure 27:
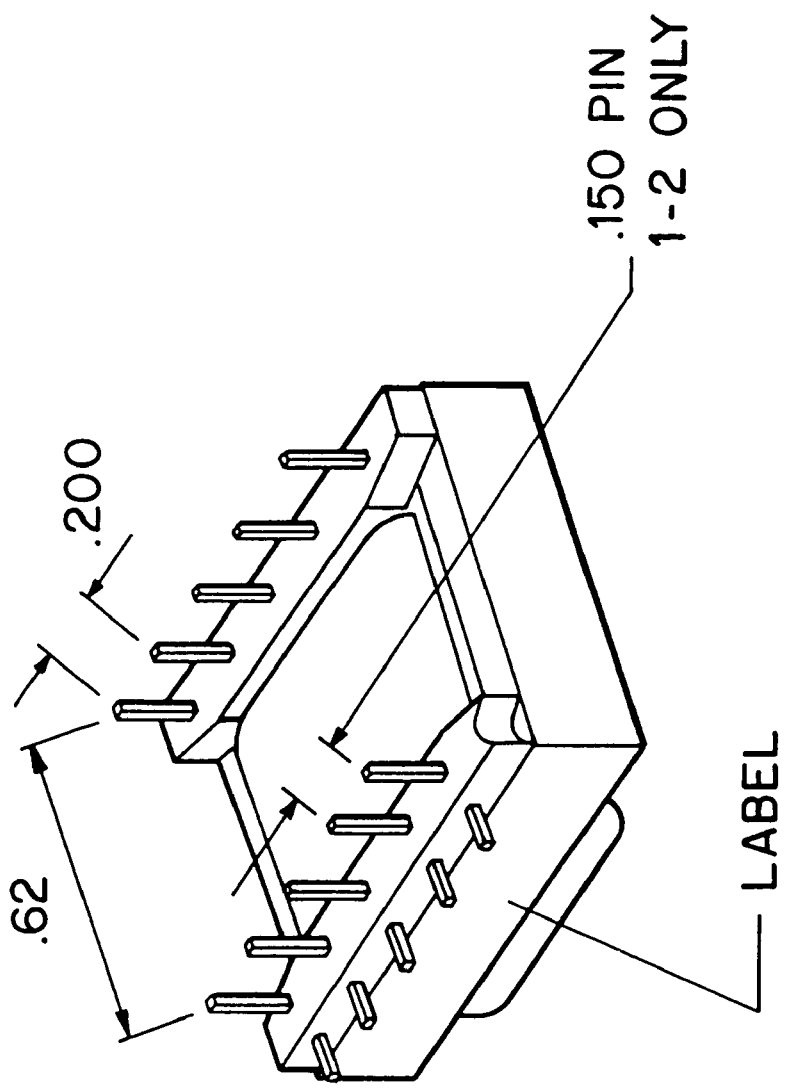
FIG. 27 is a perspective view of a transformer of the circuit diagram of FIG. 25.

The flashtube 202 is mounted on a printed circuit board 212. The board 214 includes control unit 215. The control unit 215 has a trigger circuit 216, a main discharge circuit 218. The flashtube 202 rests within a reflector 219 similar to reflector 121. The flashtube 202 is mounted axially within the reflector 203 for the longest focal range of optimum light emission as the flashtube 202 has an elongate profile. The flashtube 202 is mounted axially within the reflector 203 with the flashtube 202 centered on the reflector 219 focal point to achieve a bright circular beam of light. As the flashcube 202 moves up or down the axis the center intensity is not increased or decreased but the beam diameter will increase. As the flashtube 202 moves off axis the beam intensity will decrease and the circular beam becomes egg shaped. If the flashtube 202 is mounted across the axis of the reflector 203 the beam is oval and the flashtube 202 must be centered on the reflector focal point, A slight movement away from the focal point will not only greatly reduce he beam intensity but also result in a dark hole in the center of the beam. The axial lamp therefore provides the greatest tolerance for lamp position in the reflector 219 with an acceptable beam. The reflector 203 can be mounted to the circuit board 114 in any suitable manner, for example, using standoffs. An example of a circuit diagram for the control unit 215 is shown in FIG. 25. The control unit 215 may be implemented according to other circuit designs different from that of FIG. 25. The circuit design of the example in FIG. 25 uses the parts that are listed in FIG. 26. A perspective view of a transformer 221 of the example circuit design of FIG. 25 is shown in FIG. 27.

The control unit 215 causes the flashtube 202 to emit light. The light will be emitted as a series of pulses. The duration between pulses of light may be relatively long (>3 seconds), in a middle range (<3 seconds, >0.5 seconds) or short (<0.5 seconds). The duration may be sufficiently short that the pulses appear to join together to cause virtually constant light. The selection of the duration between pulses will depend on the selected characteristics of the system 200, including such factors as flashtube life, efficiency, available components and energy usage. Other factors include optimum visibility of the light emitted from the fluorescent material.

The operation of electronic flashtubes 202 and suitable trigger circuits 216 and main discharge circuits is discussed in the EG&G Heimann Optoelectronics GMBM catalog for August 1994 version e/712/044 100/\08.94 MVA wicker design. These materials are herein incorporated by reference.

Flashtubes are usually designed for very short on times and extinguish very quickly. As a result, the pulse frequency can also be relatively short; while, still providing the benefits of flashing, namely; having re-emitted pulses from the fluorescent material that are detectable from one another by the naked eye.

The switch 109/control unit 215 combination can incorporate a momentary mode in addition to a continuous on mode. This momentary mode would turn off the system 200 when the switch is released rather than waiting for the switch to be actuated a second time. This can beneficial in reducing the number of times the flashtube flashes (a significant factor in flashtube life). It also reduces power drain and the risk that the system will be unintentionally left on indefinitely. This feature can also be incorporated in the systems 1 and 101. The lens 113 when used in conjunction with the system 200 provides particular clarity to the re-emitted pulses as minimal visible light is emitted from the system 200 to interfere with the operator's vision; however, it is not absolutely necessary to use such a lens 113 in order to obtain many of the benefits provided by utlizing a flashtube 202 in the system 200. For example, a standard absorption filter as described earlier may be used with the system 200. Other elements of the system 200 are similar to those of the system 101; accordingly, the same reference numerals are used and the previous descriptions apply. The system 200 with flashtube 202 can provide many advantages. Xenon flashtubes tubes 202 provide significantly more ultraviolet light than Halogen incandescent bulbs, although less than fluorescent bulbs. Flashtubes 202 and control units 214 are relatively inexpensive and easy to obtain or design. Existing control units for strobing lights include a variable pulse frequency feature. They can be further simplified to provide for a fixed flashing rate to further reduce cost; as, one flashing rate will generally be suitable for most NDT or leak detection operations. The flashtubes 202 have excellent on/off characteristics for light control over the termination of one pulse and the start of another.

Greater efficiency allows for higher ultraviolet emission for the same input energy, and/or, cooler operation and lower power consumption for similar ultraviolet output with lower power consumption, extended battery operation is possible or, alternatively, smaller batteries for a lighter, more compact unit. The batteries can actually be incorporated into the system itself rather than separately from it. Rechargeable batteries may be usable.

The casing for the system 200 can be made from non-thermoset plastic to take advantage of the cooler operating temperature. This further reduces the overall cost of the system 200. Due to the overall efficiency of the system 200, a 3 watt Xenon flashtube 202 was found to be suitable for NDT uses. In order to fit within the dimensions for the reflector 219, the flashtube are length was selected as 10 mm. The reflector 219 can be made even smaller: however, the focal point may not be as forgiving in the placement of the flashtube for best operation.

A non-quarz (hard glass) flashtube was used to limit potentially harmful UVB output. This also limits the wattage to approximately 5 watts or less. If quartz is used in the flashtube the output could be raised to approximately 10 watts or less for the same arc length. The low wattage flashtube 202 results in a far lower operating current for the Xenon system 200 then the equivalent halogen filament bulb system; approximately 300 mA for the Xenon system 100 versus 4.5A for the halogen bulb system.

The low current drain provides for the possibility of continued operation from small rechargeable batteries for more than one hour. This allows for rechargeable batteries to be used in practical applications.

The cooler running Xenon system 200 is safer for the operator. As well, the system 200 makes the use of an inexpensive plastic base layer for the reflector 219 a practical alternative to aluminum. The reflector 219 coatings can be a lower temperature coating than more expensive high temperature coatings required for halogen bulbs or mercury vapour discharge lamps. Servicing and storage of the Xenon flashtube system 200 does not have to wait any significant time for the system 200 to cool down.

Xenon flashtubes 202 do not suffer from the same tendency as halogen bulbs to burn out due to overvoltages.

Overvoltages can be intended (to increase filament bulb output); even more often they can be unintended (due to increased operating voltage in automotive applications where the car is at the time). Current limiting will not typically be required to prevent reduction in bulb life.

The flashtubes 202 are more reliable when subjected to knocks and bangs than filament bulbs as there is no filament to break.

Figure 24:
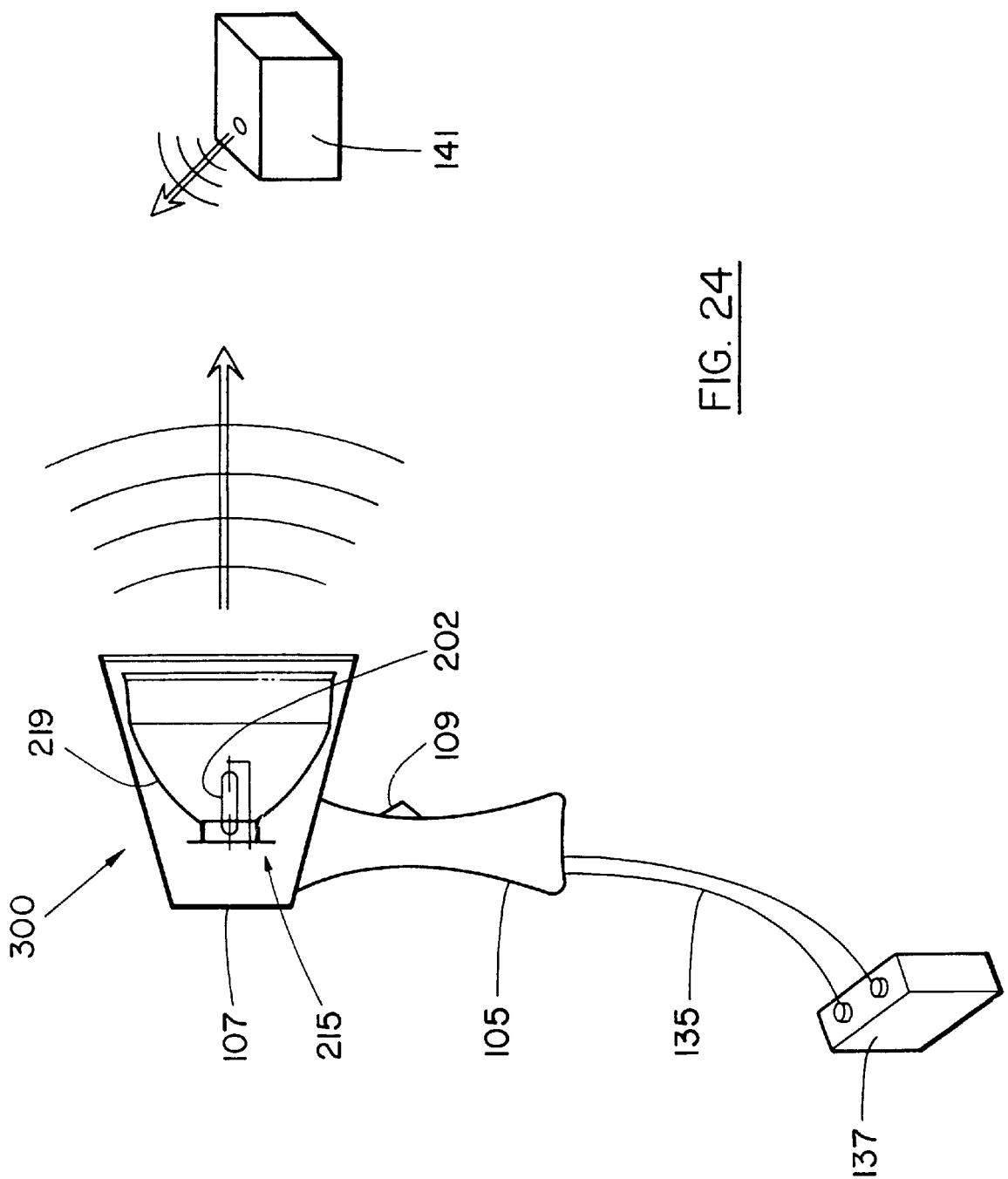
FIG. 24 is a cross-section of the alternate system of FIG. 18 employing the flashtube, reflector and control unit of FIGS. 20 and 23.

Although it is preferred to use a D battery flashlight, profile system 200 with an isotropic dichroic lens 113, it is possible to use other configurations; for example, the lamp profile 300 of FIG. 24, and/or a standard absorption filter.

It will be understood by those skilled in the art that this description is made with reference to the preferred embodiment and that it is possible to make other embodiments employing the principles of the invention which fall within its spirit and scope as defined by the following claims.

We claim:

1. A method for detecting faults in a body, comprising the steps of:
    applying a fluorescent material to the body in a manner to concentrate the fluorescent material in a pattern indicative of the location of a fault in the body;
    activating a pulsed light source to emit pulsed ultraviolet output;
    filtering light from the pulsed light source through a dichroic filter which reflects more visible light than the lens absorbs and which transmits more ultraviolet light than it absorbs or reflects;
    shining the pulsed ultraviolet light transmitted from the filter on to the body to fluoresce the fluorescent material pattern; and
    detecting faults by the fluorescence of the fluorescent material pattern indicative of the location of the faults in the body.

2. The method of claim 1, comprising the step of flashing the ultraviolet light at some time prior to shining the ultraviolet light on the body, the flashing at a rate that causes the fluorescent material to produce corresponding fluorescent flashes which flashes are detectible to the human eye.

3. The method of claims 1 or 2 wherein the light source comprises a flashtube.

4. The method of claims 1 or 2 wherein the light source comprises a high pressure arc lamp Xenon flashtube.

5. A method for detecting faults in a body, comprising the steps of:
    applying a fluorescent material to the body in a manner to concentrate the florescent material in a pattern indicative of the location of a fault in the body;
    activating a pulsed flashtube light source to emit pulsed ultraviolet output;
    filtering light from the light source through a dichroic filter that provides for the transmission of more pulsed ultraviolet light than visible light;
    shining the pulsed ultraviolet light transmitted from the filter on to the body to cause the fluorescent pattern to fluoresce; and
    detecting faults in the body by the fluorescence of the fluorescent material pattern.

6. The method of claims 5 wherein the flashtube comprises a high pressure arc lamp Xenon flashtube.

7. A system for use with a body to be tested for faults using fluorescent material, the system comprising:
    a casing,
    a reflector,
    a pulsed ultraviolet bulb which pulses at a frequency to cause the fluorescent material to pulse at a frequency which is detectable by the human eye, and
    a dichroic lens,
    wherein the casing has an open end in which the reflector rests, the pulsed ultraviolet bulb sits within the reflector in such a manner to direct light emitted from the pulsed ultraviolet bulb through the open end of the casing, and the dichroic lens encloses the open end of the casing in order to reflect into the system substantially more visible light than the lens absorbs and to transmit from the system substantially more pulsed ultraviolet light than the lens absorbs or reflects.

8. The system of claim 7, wherein the lens comprises an isotropic dichroic filter.

9. The system of claim 8, further comprising a control unit to flash the bulb at a rate that causes the fluorescent material to produce corresponding fluorescent flashes which are detectable to the human eye.

10. The system of claim 7, 8 or 9 wherein the bulb comprises a flashtube.

11. The system of claim 7, 8 or 9 wherein the flashtube comprises a high pressure arc lamp Xenon flashtube.

12. A system for use with a body to be tested for faults using fluorescent material, the system comprising:
    a handheld casing,
    a reflector,
    a high pressure arc lamp pulsed ultraviolet flashtube, said flashtube being less than or equal to 10 watts, and
    a dichroic lens,
    wherein the casing has an open end in which the reflector rests, the pulsed ultraviolet flashtube sits within the reflector in such a manner to direct light emitted from the flashtube through the open end of the casing, and the dichroic lens encloses the open and of the casing in order to transmit from the system substantially more pulsed ultraviolet light than visible light.

13. The system of claim 12, wherein the passband of the filter includes the UVA range.

14. The system of claim 13, wherein the passband of the filter substantially limits the transmission of visible and ultraviolet wavelengths outside the UVA range.

15. The system of claim 12, further comprising a control unit to flash the flashtube at a rate that causes the fluorescent material to produce corresponding fluorescent flashes which flashes are detectable to the human eye.

16. The system of claim 15, wherein the control unit is contained within the casing.

17. The system of claim 16, wherein the control unit flashes the lamp at a fixed rate.

18. The system of claim 12, wherein the system draws approximately 300 mA of current from a 12 volt power source.

19. The system of claim 12, wherein the system is operated from battery power contained within the casing.

20. The system of claim 19, wherein the battery power is rechargeable.

21. The system of claim 20, wherein the casing has a D-type battery profile.

22. The system of claim 12, wherein the reflector focusses the emitted light in a spot beam at a selected distance from the system.

23. The system of claim 22, wherein the selected distance is approximately 18 inches.

24. The system of claim 23, wherein the beam is approximately 200 mm in diameter at the selected distance.

25. The system of claim 12, wherein the flashtube is mounted axially within the reflector and centered on the reflector focal point.

26. The system of claim 12, wherein the reflector is formed from non-high temperature plastic finished with an ultraviolet reflecting finish and a non-ultraviolet absorbing protective coating.

27. The system of claim 12, wherein the reflector is finished with aluminum and coated with a non-ultraviolet absorbing coating.

28. The system of claims 26 or 27, wherein the coating comprises silicon oxide.

29. The system of claims 26 or 27, wherein the coating comprises silicon dioxide.

30. The system of claim 26, wherein the plastic comprises a non-thermoset plastic.

31. The system of claim 12, wherein the flashtube comprises a hard glass flashtube.

32. The system of claim 12, wherein the flashtube is an approximately 5 watt or less flashtube.

33. The system of claim 12, wherein the flashtube is a 3 watt flashtube.

34. The system of claim 12, wherein the casing is formed from non-high temperature plastic.

35. The system of claim 12, wherein the system is not hot to the touch during operation.

* * * * *